(12) United States Patent
Omata et al.

(10) Patent No.: US 11,507,649 B2
(45) Date of Patent: *Nov. 22, 2022

(54) OPTICAL FINGERPRINT AUTHENTICATION DEVICE

(71) Applicant: Merck Patent GmbH, Darmstadt (GE)

(72) Inventors: Kazuyoshi Omata, Kofu (JP); Tsukasa Yagi, Kobe (JP); Natsuki Yamamoto, Kawasaki (JP); Hirofumi Ohtani, Hino (JP)

(73) Assignee: MERCK PATENT GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/038,489

(22) Filed: Sep. 30, 2020

(65) Prior Publication Data

US 2021/0011987 A1 Jan. 14, 2021

Related U.S. Application Data

(63) Continuation of application No. 16/060,532, filed as application No. PCT/JP2016/075651 on Sep. 1, 2016, now Pat. No. 10,853,465.

(30) Foreign Application Priority Data

Dec. 8, 2015 (JP) .............................. JP2015-239048

(51) Int. Cl.
G06F 21/32 (2013.01)
G06T 1/00 (2006.01)
G06V 40/13 (2022.01)
G06V 40/12 (2022.01)
A61B 5/1172 (2016.01)
H05B 33/28 (2006.01)
(Continued)

(52) U.S. Cl.
CPC ............ G06F 21/32 (2013.01); A61B 5/1172 (2013.01); G06T 1/00 (2013.01); G06V 40/1318 (2022.01); G06V 40/1365 (2022.01); H01L 27/3225 (2013.01); H01L 51/50 (2013.01); H01L 51/5012 (2013.01); H01L 51/5203 (2013.01); H01L 51/5246 (2013.01); H05B 33/28 (2013.01)

(58) Field of Classification Search
CPC .. G06F 21/32; G06K 9/0004; G06K 9/00087; H01L 27/3225; H01L 51/5012; H01L 51/5203; H01L 51/5246
See application file for complete search history.

(56) References Cited

U.S. PATENT DOCUMENTS 10,176,355 B2 * 1/2019 Smith .................. G06K 9/0008
2008/0317303 A1 * 12/2008 Konno ................. G06K 9/2027
382/124

(Continued)

Primary Examiner — Utpal D Shah
(74) Attorney, Agent, or Firm — Lucas & Mercanti, LLP

(57) ABSTRACT

An optical fingerprint authentication device includes at least a light source and an image sensor and detects diffused light. The light source is an organic electroluminescence panel. The organic electroluminescence panel comprises a light emitting portion region and a light-transmitting non-light emitting portion, the light emitting portion region being shaped by an organic electroluminescence element. A fingerprint information reader having the image sensor arranged at a position adjacent to the non-light emitting portion is provided.

17 Claims, 11 Drawing Sheets

(51) Int. Cl.
  *H01L 51/50* (2006.01)
  *H01L 27/32* (2006.01)
  *H01L 51/52* (2006.01)

(56) References Cited

U.S. PATENT DOCUMENTS

| | | | | |
|---|---|---|---|---|
| 2012/0256089 | A1* | 10/2012 | Kanda | G01J 1/44 250/206 |
| 2016/0172426 | A1* | 6/2016 | Kim | H01L 51/56 257/40 |
| 2017/0017824 | A1* | 1/2017 | Smith | G02B 5/005 |

\* cited by examiner

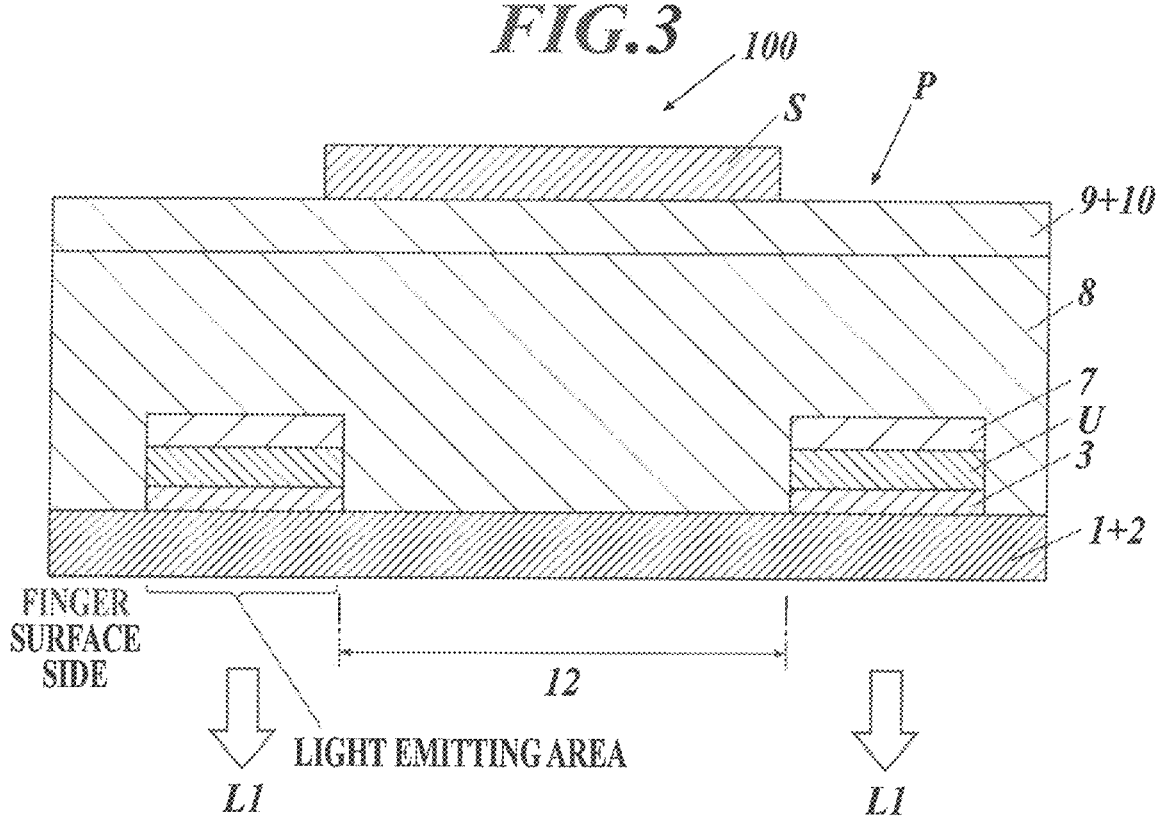
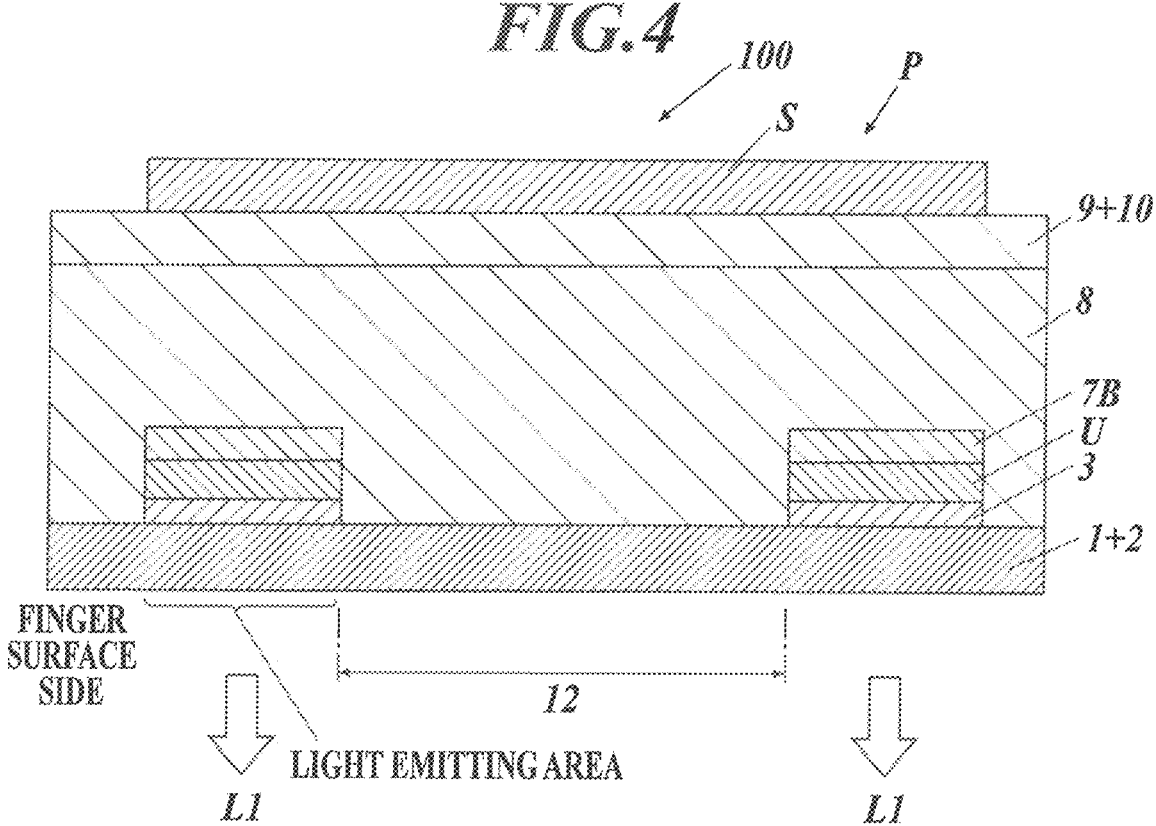

OPTICAL FINGERPRINT AUTHENTICATION DEVICE

CROSS REFERENCE TO RELATED APPLICATION

This application is a continuation of U.S. patent application Ser. No. 16/060,532 filed Jun. 8, 2018, which in term was a 371 of PCT/JP2016/075651 filed on Sep. 1, 2016, which, in turn, claimed the priority of Japanese Patent Application No. JP 2015-239048 filed on Dec. 8, 2015, all of the above applications are incorporated herein by reference.

TECHNOLOGICAL FIELD

The present invention relates to an optical fingerprint authentication device which performs personal authentication with fingerprint by optical method. More specifically, the present invention relates to an optical fingerprint authentication device provided with a fingerprint information reader including an organic electroluminescent element which is used as a light source for illumination.

DESCRIPTION OF THE RELATED ART

In recent years, the need of personal authentication with a biological pattern such as a fingerprint, vein, voiceprint, or iris of a user is increasing as one of the method for specifying the user by an ATM (Automated Teller Machine) in a bank, a cellular phone, a PDA (Personal Data Assistant), a personal computer, and the like. Among these, the fingerprint is used in the oldest and proven biometric authentication method. A fingerprint input device using a total reflection prism is practically used for a long time, however, such device is not easily miniaturized or suitable for mobile devices such as a laptop, PDA, and a cellular phone. Therefore, thinned and miniaturized fingerprint input devices are variously disclosed.

For example, Japanese patent No. 3684233 discloses a light emitting diode (hereinafter abbreviated as LED) arranged as a light source for illumination adjacent to a solid imaging element on a wiring substrate for an fingerprint pattern authentication method by causing a light emitted from the LED for illumination to enter into a finger and by causing the scattered light to be transmitted through a fingerprint and to enter into the solid imaging element.

Japanese Patent Application Laid Open Publication No. 2005-18595 discloses an LED for illumination arranged adjacent to a solid imaging element for a fingerprint pattern authentication method by causing the light emitted from the LED for illumination to enter into a finger through a protective member and causing the scattered light to be transmitted through a fingerprint and the protective member and to enter into the solid imaging element.

Japanese Patent Application Laid Open Publication No. 2003-233805 and Japanese Patent Application Laid Open Publication No. 2005-38406 disclose a circuit substrate having an image sensor (solid imaging element) and a protective member laminated thereon. The disclosed method includes adhesion of a finger to the surface of the protective member, arranging an LED for illumination on the circuit substrate and adjacent to a light sensor, and irradiating the finger with the light through a light guide.

Patent document 1 discloses a fingerprint input device which includes an LED used as a light source for illumination and, while moving a finger and an imaging element relative to each other, imaging a fingerprint pattern generated by the scattered light in the finger by the imaging element.

Patent document 2 discloses an optical fingerprint input device which irradiates a finger surface with the light from an LED and receives the reflected light from the finger surface by an imaging element. An imaging chip having a specific structure is provided in the proposed structure.

However, since each fingerprint authentication device proposed as above includes an LED used as a light source for illumination, an illumination unit requires to incorporate a light guide plate and the like. This results in a thick structure and thus causes a significant trouble from the viewpoint of providing a thin device. Furthermore, due to the structure of an LED, there is a problem of difficulty in processing the LED into a shape having a curved surface, such as a round shape or an elliptic shape.

PRIOR ART DOCUMENT

Patent Document

[Patent Document 1] Japanese Patent Application Laid Open Publication No. 2007-328511
[Patent Document 2] Japanese Patent Application Laid Open Publication No. 2005-118289

SUMMARY

Problems to be Solved by the Invention

The present invention is conceived in view of the above problems, and the object to be solved is to provide an optical fingerprint authentication device which includes an organic electroluminescence panel applied as a light source for illumination, has a thin structure, and is provided with a fingerprint information reader having various shapes of light source for illumination according to purposes.

Means for Solving the Problem

As a result of intensive studies by the inventors in view of the problems described above, it was found that an optical fingerprint authentication device having a thin structure and various shapes of a light source for illumination according to purposes can be obtained by providing an optical fingerprint authentication device which has at least a light source and an image sensor and detects diffused light, wherein an organic electroluminescence panel (hereinafter also referred to as an organic EL panel) is used as the light source, the organic EL panel includes a light emitting portion region which is shaped by an organic electroluminescence element (hereinafter also referred to as an organic EL element) and a light-transmitting non-light emitting portion, and a fingerprint information reader having the image sensor arranged at a position adjacent to at least the non-light emitting portion.

That is, the above-described problems of the present invention are solved by the following means.

To achieve at least one of the abovementioned objects, according to an aspect of the present invention, an optical fingerprint authentication device which includes at least a light source and an image sensor and detects diffused light,
wherein the light source is an organic electroluminescence panel,
wherein the organic electroluminescence panel includes a light emitting portion region and a light-transmitting non-light emitting portion, the light emitting portion region being shaped by an organic electroluminescence element; and wherein a fingerprint information reader having the image sensor arranged at a position adjacent to the non-light emitting portion is provided.

Advantageous Effects of Invention

According to the present invention, it is possible to provide an optical fingerprint authentication device having a thin structure and provided with a fingerprint information reader having various shapes of light source for illumination according to purposes.

The technical features of the optical fingerprint authentication device defined in the present invention and the way how it exhibits advantageous effects are estimated as follows.

An LED, which is advantageous regarding life as a light source, is widely used as a light source for illumination in a conventional optical fingerprint authentication device as described above, however, raises problems such as a thick structure and difficulty in processing into various shapes, due to the principle of light emission.

As a method for solving such problems, the present inventors have found that the above-described problems can be solved by applying an organic electroluminescence panel provided with an organic EL element as a light source That is, while utilizing the features of an organic EL element, which is a thin-film light emitting element, the formation method thereof (for example, a chemical vapor deposition method or a wet application method) allows to form an organic EL element having an arbitrary light emission pattern, so that it is possible to design fingerprint information readers having a detection area of various shapes required for the optical fingerprint authentication device, and to correspond to fingerprint authentication devices for various needs. Furthermore, it is possible to improve the recognition rate by the fingerprint authentication device by achieving a light source for illumination with uniform light having various shapes.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 3 is a schematic cross-sectional view showing an exemplary structure of an organic EL panel which can be applied to the present invention (Embodiment 1).

FIG. 4 is a schematic cross-sectional view showing another exemplary structure of an organic EL panel which can be applied to the present invention (Embodiment 2).

DETAILED DESCRIPTION OF EMBODIMENTS

Figure 1:
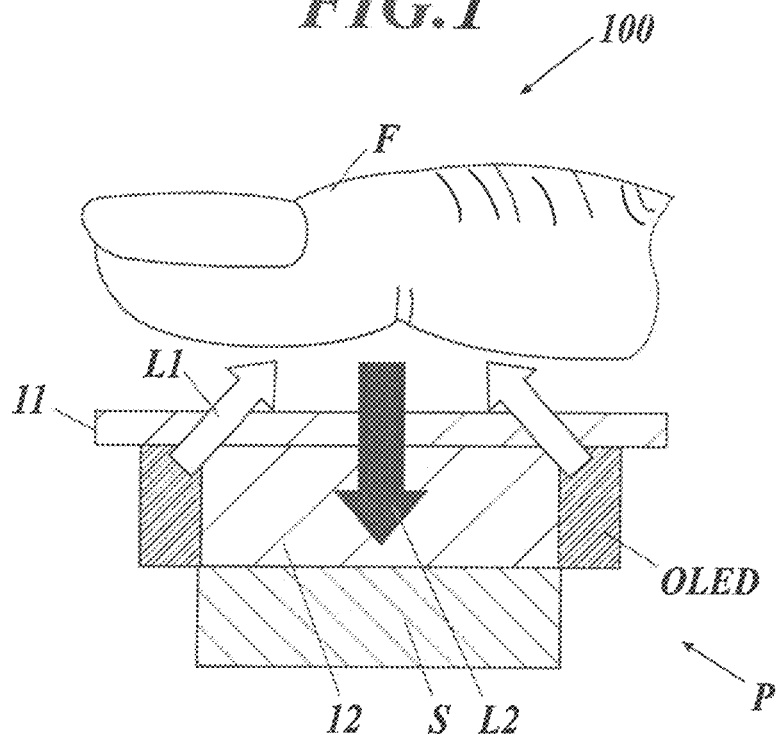
FIG. 1 is a schematic view showing an example of an entire structure of a fingerprint information reader constituting an optical fingerprint authentication device of the present invention.

Hereinafter, one or more embodiments of the present invention will be described with reference to the drawings. However, the scope of the invention is not limited to the disclosed embodiments.

According to the present invention, it is possible to provide an optical fingerprint authentication device having a thin structure and provided with a fingerprint information reader having various shapes of light source for illumination according to purposes.

The technical features of the optical fingerprint authentication device defined in the present invention and the way how it exhibits advantageous effects are estimated as follows.

An LED, which is advantageous regarding life as a light source, is widely used as a light source for illumination in a conventional optical fingerprint authentication device as described above, however, raises problems such as a thick structure and difficulty in processing into various shapes, due to the principle of light emission.

As a method for solving such problems, the present inventors have found that the above-described problems can be solved by applying an organic electroluminescence panel provided with an organic EL element as a light source.

That is, while utilizing the features of an organic EL element, which is a thin-film light emitting element, the formation method thereof (for example, a chemical vapor deposition method or a wet application method) allows to form an organic EL element having an arbitrary light emission pattern, so that it is possible to design fingerprint information readers having a detection area of various shapes required for the optical fingerprint authentication device, and to correspond to fingerprint authentication devices for various needs. Furthermore, it is possible to improve the recognition rate by the fingerprint authentication device by achieving a light source for illumination with uniform light having various shapes.

The optical fingerprint authentication device of the present invention has at least a light source and an image sensor and provided with a fingerprint information reader to detect diffused light. As the light source is included an organic electroluminescence panel which includes a light emitting portion region shaped by an organic electroluminescence element and a light-transmitting non-light emitting portion. The image sensor is arranged at a position adjacent to the non-light emitting portion. These features are technical features commonly owned by the invention recited in each claim.

As an embodiment of the present invention, from the viewpoint of exhibiting objective effects of the present invention further, the organic EL element preferably includes an organic functional layer unit between a pair of electrodes facing each other. One of the electrodes is a light-transmitting electrode and the other is a non-light transmitting electrode, so that only one of the surface sides is the light emitting surface. Such structure is preferred in that the fingerprint detector is efficiently irradiated with irradiation light and that the image sensor can receive light with enhanced sensitivity.

Alternatively, according to the structure of the organic EL panel, the organic EL element may include the pair of electrodes facing each other which are both light-transmitting electrodes, so that the organic EL element is designed to be a both-face light emission type.

Preferably, transparent electrode(s) included in the organic EL element includes an oxide semiconductor or a thin film of a metal or an alloy, in that electrode(s) having both high light transmittance and excellent conductivity can be obtained.

Preferably, at the light-transmitting non-light emitting portion is formed a light-transmitting electrode or are provided a light-transmitting electrode and an organic functional layer unit, so that the method of manufacturing an optical fingerprint authentication device becomes easier.

According to preferred arrangement patterns of the organic EL element of the organic EL panel included in the optical fingerprint input device of the present invention, the organic EL element may be arranged at the peripheral portion of a elliptic shape to form a light-transmitting non-light emitting portion at the center portion, or a plurality of strip-shaped organic EL elements may be arranged separately in parallel to form a light-transmitting non-light emitting portion between the organic EL elements, in that optical information required for fingerprint authentication can be efficiently acquired.

Preferably, the organic electroluminescence panel is designed to emit light which has a wavelength in a visible light region or light which has a wavelength in an infrared region, in that the usage can be expanded.

The "organic EL panel" according to the present invention indicates a structure including the light emitting portion region shaped by the organic EL element and the light-transmitting non-light emitting portion on the same plane.

The "organic EL element" according to the present invention indicates a surface light source which irradiate a specimen surface (specifically, a fingerprint surface) with light for fingerprint authentication. Mainly on a transparent base material are provided a pair of light-transmitting electrodes facing each other (an anode and a cathode) or a pair of electrodes which are constituted by a light-transmitting electrode and a non-light-transmitting electrode, an organic functional layer unit between the pair of electrodes constituted by a carrier transporting functional layer which mainly controls the transportation of electrons or holes and a light emitting layer, and a sealing member further provided thereon. However, for convenience of explanation, the description or explanation of the sealing member is omitted in some cases. Furthermore, in the detailed description of embodiments of the present invention described below, control circuits and wires to control light emission from the organic EL element are omitted.

The "organic functional layer unit" according to the present invention is explained with reference to FIG. 2 detailed below, and exemplified by a structure including a first carrier transporting functional layer group 1 (for example, a hole injecting layer, a hole transporting layer, and the like), a light emitting layer including a phosphorescent material and the like, and a second carrier transporting functional layer group 2 (for example, a hole blocking layer, electron transporting layer, electron injecting layer, and the like) which are arranged in layers on a base material.

The "light emitting area" according to the present invention indicates a region in which all of the anode, the organic functional layer unit, and the cathode exist when viewed in the thickness direction.

The "anode" according to the present invention is also referred to as the "first electrode" and indicates an electrode to apply (+) as a voltage. The "cathode" according to the present invention is also referred to as the "second electrode" and indicates an electrode to apply (−) as a voltage.

The "light transmittance" according to the present invention indicates that the light transmission rate at the wavelength of 550 nm is 60% or more, preferably 70% or more, more preferably 80% or more. The "no light transmittance" indicates that the light transmission rate at the wavelength of 550 nm is 40% or less, preferably 30% or less, more preferably 20% or less.

Hereinafter, components of the present invention and embodiments to carry out the present invention will be described in detail with reference to the drawings. Throughout the specification, "to" representing a range of numerical values is used to indicate that the values described before and after "to" are respectively included as the lower limit and the upper limit. Numeral codes in each drawing are represented by numbers in parentheses at the end of the components in the explanation of each drawing.

<<Basic Structure of Optical Fingerprint Authentication Device>>

The optical fingerprint authentication device according to the present invention mainly includes a light source and an image sensor. The light source is an organic EL panel constituted by a light emitting portion region and a light-transmitting non-light emitting portion. The light emitting portion region is constituted by an organic EL element. The optical fingerprint authentication device is provided with a fingerprint information reader with the image sensor arranged at a position adjacent to the non-light emitting portion.

FIG. 1 is a schematic diagram showing an example of entire structure of a fingerprint information reader included in an optical fingerprint authentication device of the invention.

As the fingerprint information reader (100) of the optical fingerprint authentication device shown in FIG. 1, there are provided an organic EL panel (P) which is constituted by organic EL elements (OLEDs) and a light-transmitting non-light emitting portion (12), and an image sensor (S) which is arranged below the light-transmitting non-light emitting portion (12) and optically reads fingerprint information of a specimen. 11 is a glass substrate to hold a finger (F).

The organic EL elements (OLEDs) as light sources constituting the organic EL panel (P) emit light (L1, also referred to as irradiation light) and irradiate the fingerprint surface of the finger (F) with the light (L1). The reflection light (L2, also referred to as a light signal) from the finger surface is transmitted through the light-transmitting non-light emitting portion (12) of the organic EL panel (P). Optical information is read by the image sensor (S) and, though not shown in the drawings, image information read by the image sensor (S) is analyzed and compared with the stored (registered) fingerprint information by the image sensor (S) to perform fingerprint authentication.

The image sensor (S) applied to the optical fingerprint authentication device according to the present invention is also referred to as a solid imaging element and may be, for example, an image sensor of a CCD (Charge Coupled Device) type or a CMOS (Complementary Metal Oxide Semiconductor) type <<Basic Structure of Organic EL Element>>

Next, with reference to the drawings will now be described basic structures of the organic EL element constituting the organic EL panel according to the present invention.

Figure 2:
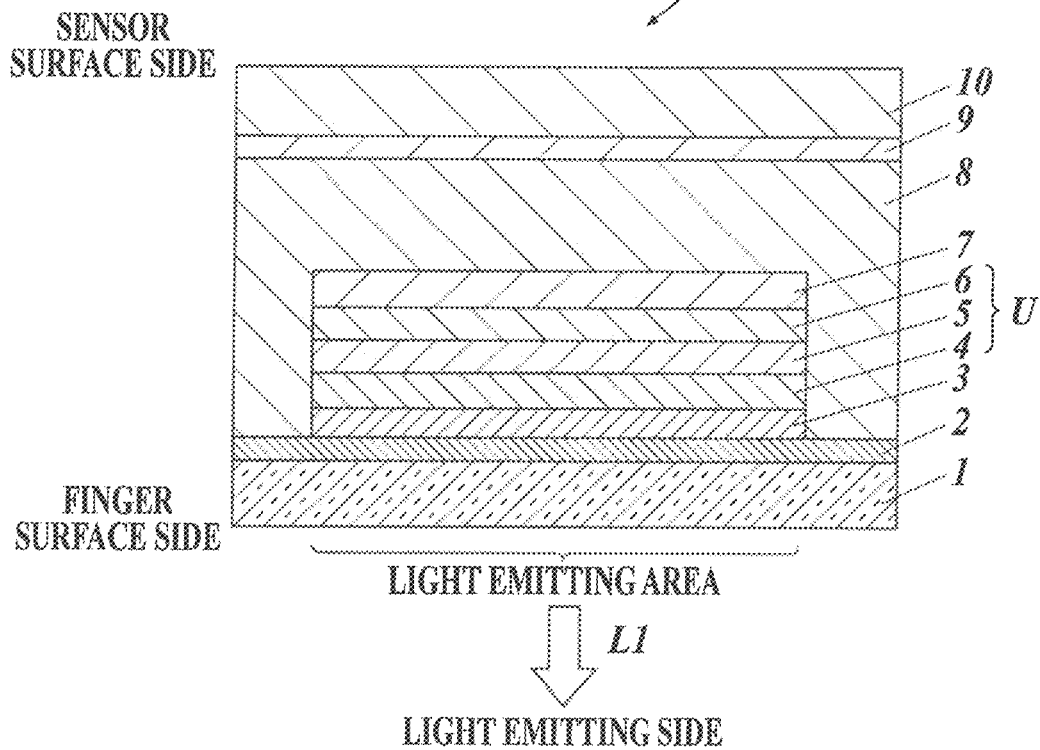
FIG. 2 is a schematic cross-sectional view showing an exemplary structure of an organic EL element which can be applied to the present invention.

FIG. 2 is a schematic cross-sectional view showing a basic structure of an organic EL element including the organic functional layer unit which can be applied to the present invention.

The organic EL element (OLED) according to the present invention shown in FIG. 2 has a structure in which an organic functional layer unit (U) including a light emitting layer is laminated on a transparent substrate (1) having light transmittance, such as a glass substrate or a flexible resin substrate, According to the example shown in FIG. 2, a gas barrier layer (2) is formed on the transparent substrate (1) having light transmittance. An organic functional layer unit (U) is constituted by the anode (3) formed as a first electrode on the gas barrier layer (2), on which sequentially laminated are the first carrier transporting functional layer group 1 (4) constituted by, for example, the hole injecting layer, the hole transporting layer, and the like, the light emitting layer (5), and the second carrier transporting functional layer group 2 (6) constituted by, for example, the electron transporting layer, the electron injecting layer, and the like. Furthermore, above the organic functional layer unit (U) is provided a cathode (7) as the second electrode. The organic EL element (OLED) is formed by providing a sealing substrate (10) having a sealing adhesion layer (8) and a gas barrier layer (9) and covering the above-described entire laminate.

According to the structure shown in FIG. 2, the anode (3) as the first electrode is the transparent electrode having light transmission rate defined above, and the cathode (7) as the second electrode is an electrode having no light transmittance. In an exemplary method, light irradiation (L1) of the finger (F) is performed from a finger surface side, on which the anode (3) is arranged.

As shown in FIG. 2, a light emitting area is defined as a region in which all of the anode (3), the organic functional layer unit (U), the light emitting layer (5) in particular, and the cathode (7) are present in a single plane.

[Component of Organic EL Element]

First of all, the details of main components of the organic EL element constituting the organic EL panel according to the present invention are explained.

In the organic EL element (OLED) according to the present invention, as explained with reference to FIG. 2, a light emitting region is constituted by laminating, on the transparent substrate (1) having the gas barrier layer (2), the light-transmitting anode (3) as the first electrode, the carrier transporting functional layer group 1 (4) constituted by, for example, the hole injecting layer and the hole transporting layer, the light emitting layer (5), and the carrier transporting functional layer group 2 (6) constituted by, for example, the electron transporting layer and the electron injecting layer. The cathode (7) and the sealing substrate (10) having the sealing adhesive layer (8) and the gas barrier layer (9) are further provided thereon.

Typical structure of the organic EL element is shown below:

(i) Anode having light transmittance (3)/Organic functional layer unit (U) [Carrier transporting functional layer group 1 (4: Hole injecting transporting layer)/Light emitting layer (5)/Carrier transporting functional layer group 2 (6: Electron injecting transporting layer)]/Cathode having no light transmittance (7)

(ii) Anode having light transmittance (3)/Organic functional layer unit (U) [Carrier transporting functional layer group 1 (4: Hole injecting transporting layer)/Light emitting layer (5)/Carrier transporting functional layer group 2 (6: Hole blocking layer/Electron injecting transporting layer)]/Cathode having no light transmittance (7)

(iii) Anode having light transmittance (3)/Organic functional layer unit (U) [Carrier transporting functional layer group 1 (4: Hole injecting transporting layer/Electron blocking layer)/Light emitting layer (5)/Carrier transporting functional layer group 2 (6: Hole blocking layer/Electron injecting transporting layer)]/Cathode having no light transmittance (7)

(iv) Anode having light transmittance (3)/Organic functional layer unit (U) [Carrier transporting functional layer group 1 (4: Hole injecting layer/Hole transporting layer)/Light emitting layer (5)/Carrier transporting functional layer group 2 (6: Electron transporting layer/Electron injecting layer)]/Cathode having no light transmittance (7)

(v) Anode having light transmittance (3)/Organic functional layer unit (U) [Carrier transporting functional layer group 1 (4: Hole injecting layer/Hole transporting layer)/Light emitting layer (5)/Carrier transporting functional layer group 2 (6: Hole blocking layer/Electron transporting layer/Electron injecting layer)]/Cathode having no light transmittance (7)

(vi) Anode having light transmittance (3)/Organic functional layer unit (U) [Carrier transporting functional layer group 1 (4: Hole injecting layer/Hole transporting layer/Electron blocking layer/Light emitting layer (5)/Carrier transporting functional layer group 2 (6: Hole blocking layer/Electron transporting layer/Electron injecting layer)]/Cathode having no light transmittance (7)

In the structures explained in (i) to (vi) above, the cathode (7) is explained to have no light transmittance, however, if necessary, the cathode may have light transmittance as well as the anode.

Further, a non-light emitting intermediate layer may be provided between the light-emitting layers. The intermediate layer may be an electron generating layer or may have a multiphoton emission structure.

The detailed structures of the organic EL elements applicable to the present invention are disclosed in, for example, Japanese Unexamined Patent Application Publication Nos. 2013-157634, 2013-168552, 2013-177361, 2013-187211, 2013-191644, 2013-191804, 2013-225678, 2013-235994, 2013-243234, 2013-243236, 2013-242366, 2013-243371, 2013-245179, 2014-003249, 2014-003299, 2014-013910, 2014-017493, and 2014-017494.

A tandem type organic EL element can also be used. Examples of a tandem type organic EL element are described in: U.S. Pat. Nos. 6,337,492, 7,420,203, 7,473,923, 6,872,472, 6,107,734, and 6,337,492, International Publication No. 2005/009087, Japanese Unexamined Patent Application Publication Nos. 2006-228712, 2006-24791, 2006-49393, 2006-49394, 2006-49396, 2011-96679, and 2005-340187, JP Patent Nos. 4711424, 3496681, 3884564, and 4213169, Japanese Unexamined Patent Application Publication Nos. 2010-192719, 2009-076929, 2008-078414, 2007-059848, 2003-272860, and 2003-045676, and International Publication No. 2005/094130. The structures of the elements and the composing materials are described in these documents, however, the present invention is not limited to them.

Individual layers constituting the organic EL element will now be described.

[Transparent Substrate]

The transparent substrate (1) applied to the organic EL element (OLED) is not particularly limited and may be any substrate having light transmittance, such as glass, plastics, and the like.

Examples of the substrate (1) having light transmittance which can be applied to the present invention include glass, quartz, and resin substrate. A flexible resin material is more preferred in that flexibility can be provided to the organic EL element.

Examples of the resin material constituting the resin substrate which can be applied to the present invention include polyesters such as poly(ethylene terephthalate) (abbreviation: PET) and poly(ethylene naphthalate) (abbreviation: PEN); polyethylene; polypropylene; cellophane; cellulose esters and derivatives thereof, such as cellulose diacetate, cellulose triacetate (abbreviation: TAC), cellulose acetate butyrate, cellulose acetate propionate (abbreviation: CAP), cellulose acetate phthalate, and cellulose nitrate; poly(vinylidene chloride); poly(vinyl alcohol); poly(ethylene-vinyl alcohol); syndiotactic polystyrene; polycarbonates (abbreviation: PC); norbornene resins; polymethylpentene; polyether ketones; polyimides, polyether sulfones (abbreviation: PES); poly(phenylene sulfide); polysulfones; polyether imides; polyether ketone imides; polyamides; fluorinated resins; nylons; poly(methyl methacrylate); acrylics and polyallylates; and cycloolefin resins, such as Arton (commercial name, available from JSR) and Apel (commercial name, available from Mitsui Chemicals, Inc.).

Among these resin materials, films of polyethylene terephthalate (abbreviation: PET), polybutylene terephthalate, polyethylene naphthalate (abbreviation: PEN), and polycarbonate (abbreviation: PC) are preferably used as resin substrates having flexibility with respect to the cost or the easy availability.

The resin substrate described above may be an unstretched film or a stretched film.

The resin substrate which can be applied to the present invention can be manufactured by a conventionally known common method for manufacturing films. For example, a resin as a material is melted by an extruder, extruded through a ring die or a T-die, and rapidly cooled, so that an unstretched resin substrate, which is substantially amorphous and is not oriented, can be produced. A stretched resin substrate can be produced by stretching the unstretched resin substrate in the moving direction of the resin substrate (longitudinal direction, MD direction) or the direction perpendicular to the moving direction of the resin substrate (lateral direction, TD direction) by a well-known method such as one axis stretching, tenter type sequential biaxial stretching, tenter type simultaneous biaxial stretching, or tubular simultaneous biaxial stretching. The stretching ratio in this case can be appropriately selected according to the resin which is the raw material of the resin substrate, and is preferably within 2 to 10 times in each of longitudinal direction and lateral direction.

The resin substrate is preferably a thin film having a thickness within the range of 3 to 200 μm, more preferably within the range of 10 to 150 μm, particularly preferably within the range of 20 to 120 μm.

Examples of the glass substrate which can be applied as the substrate having light transmittance according to the present invention include soda lime glass, barium and strontium containing glass, lead glass, aluminosilicate glass, borosilicate glass, barium borosilicate glass, and quartz.

[First Electrode: Anode]

The anode constituting the organic EL element is preferably an electrode having light transmittance and preferably includes, for example, an oxide semiconductor or a thin film of a metal or an alloy. For example, metals such as Ag and Au, alloys primarily composed of such metals, CuI, indium-tin complex oxide (ITO), and oxide semiconductors such as $SnO_2$ and ZnO.

The formation method of the anode may be, for example, a vacuum evaporation method (such as a resistance heating deposition method, an electron beam deposition method, an ion plating method, and an ion beam evaporation method), a sputtering method, a reactive sputtering method, a molecular beam epitaxy method, a plasma polymerization method, an atmospheric-pressure plasma polymerization method, a plasma CVD method, a laser CVD method, a thermal CVD method, and the like.

In the case where an anode having light transmittance is primarily composed of silver, the purity of silver is preferably 99% or more. Palladium (Pd), copper (Cu) or gold (Au) may be added in order to keep the stability of silver.

The anode having light transmittance is a layer mainly composed of silver. Specifically, it may be composed of silver alone or of an alloy including silver (Ag). Examples of such alloy include silver-magnesium (Ag—Mg), silver-copper (Ag—Cu), silver-palladium (Ag—Pd), silver-palladium-copper (Ag—Pd—Cu), and silver-indium (Ag—In).

Among the composing materials of the above-described anode, the anode constituting the organic EL element according to the present invention preferably includes silver as a main component, has a thickness within the range of 2 to 20 nm, more preferably within the range of 4 to 12 nm, and has light transmittance. A thickness of 20 nm or less is preferred because absorption and reflection of light by the anode having light transmittance can be reduced and thus high light transmittance can be maintained.

The layer primarily composed of silver according to the present invention indicates that the anode having light transmittance contains silver in the amount of 60 mass % or more, preferably 80 mass % or more, more preferably 90 mass % or more, most preferably 98 mass % or more. The "light transmittance" used for the anode having light transmittance according to the present invention indicates that the light transmission rate is 50% or more at the wavelength of 550 nm.

The anode having light transmittance may be a plurality of separate and laminated layers as needed, primarily composed of silver.

In the present invention, in the case where the anode is primarily composed of silver and has light transmittance, from the viewpoint of improving uniformity of the silver layer composing the anode having light transmittance, a ground layer is preferably arranged under the anode. The ground layer is not particularly limited as long as aggregation of silver can be suppressed while producing a film anode composed of silver or an alloy including silver as a main component. The layer preferably includes an organic compound having a nitrogen atom or a sulfur atom, for example. Preferably, the anode having light transmittance is formed on the ground layer.

[Organic Functional Layer Unit]

(Light Emitting Layer)

A phosphorescent compound or a fluorescent compound can be used as a light emitting material in the light emitting layer (5) constituting the organic EL element (OLED). In the present invention, the light emitting material preferably includes a phosphorescent compound, in particular.

Electrons injected from an electrode or the electron transporting layer and holes injected from the hole transporting layer recombine in the light emitting layer to emit light. Light may be emitted in the light emitting layer or at an interface between the light emitting layer and the adjacent layer.

The light emitting layer may have any structures, as long as the included light emitting material satisfies requirements for light emission. The light emitting layer may be composed of a plurality of layers having the same emission spectrum or the same maximum emission wavelength. In this case, a non-light emitting intermediate layer is preferably arranged between the individual light emitting layers.

The total thickness of the light emitting layer is preferably within the range of 1 to 100 nm, more preferably 1 to 30 nm to reduce the driving voltage. When a non-light emitting intermediate layer is present between the light emitting layers, the total thickness of the light emitting layer includes the thickness of the intermediate layer.

The light emitting layer described above may be formed with light emitting material(s) and host compound(s), which will be described below, by any known method, such as vacuum evaporation, spin coating, casting, LB (Langmuir-Blodgett) coating, or ink jetting.

The light emitting layer may be composed of a plurality of light emitting materials, for example, a phosphorescent material and a fluorescent material (also referred to as a fluorescent dopant or fluorescent compound) may be mixed to be used in a single light emitting layer. In a preferred embodiment, the light emitting layer includes a host compound (also referred to as a light emitting host and the like) and a light emitting material (also referred to as a light emitting dopant compound) so that the light emitting material emits light.

<Host Compound>

Preferred host compounds to be included in the light emitting layer have a phosphorescence quantum yield of less than 0.1 at room temperature (25° C.). More preferably, the phosphorescence quantum yield is less than 0.01. In the compound included in the luminous layer, the volume fraction of the host compound is preferably 50% or more.

Any known host compound may be used alone or in combination. A plurality of kinds of host compounds may be used to adjust charge transfer and thus to enhance the efficiency of the organic electroluminescent element. A plurality of light emitting materials described below may be used to mix light having different colors and thus to emit light with a desired color.

The host compounds used in the light emitting layer may be any known low molecular weight compound, any high molecular weight compound having repeating units, or any low molecular weight compound having a polymerizable group such as a vinyl group or an epoxy group (evaporation-polymerizable light emitting host).

The host compounds which can be applied to the present invention include compounds disclosed in, for example, Japanese Unexamined Patent Application Publication Nos. 2001-257076, 2001-357977, 2002-8860, 2002-43056, 2002-105445, 2002-352957, 2002-231453, 2002-234888, 2002-260861, and 2002-305083; United States Patent Application Nos. 2005/0112407 and 2009/0030202; WO 2001/039234, WO 2008/056746, WO 2005/089025, WO 2007/063754, WO 2005/030900, WO 2009/086028, and WO 2012/023947; Japanese Unexamined Patent Application Publication No. 2007-254297; and EP 2034538.

<Light Emitting Material>

Examples of the light emitting material which can be used in the present invention include phosphorescent compounds (also referred to as phosphorescent materials or phosphorescent dopants) and fluorescent compounds (also referred to as fluorescent materials). In particular, phosphorescent compounds are preferably used due to their high light emitting efficiency.

<Phosphorescent Compound>

Phosphorescent compounds are defined as compounds which emit light from the excited triplet state and, specifically, which emit phosphorescent light at room temperature (25° C.) and have a phosphorescent quantum yield of 0.01 or more at 25° C. The phosphorescent quantum yield is preferably 0.1 or more.

The phosphorescent quantum yield described above may be determined by the method described in the Fourth Series of Experimental Chemistry, Vol. 7 Spectroscopy II, page 398 (1992, published by Maruzen). The phosphorescent quantum yield in a solution may be determined with any solvent, and phosphorescent compounds having a phosphorescent quantum yield of 0.01 or more determined with any solvent may be used in the present invention.

The phosphorescent compound may be appropriately selected from any known phosphorescent compounds used in light emitting layers of common organic EL elements. Preferred are complexes containing metal atoms belonging to groups 8 to 10 in the periodic table, more preferred are iridium compounds, osmium compounds, platinum compounds (platinum-based complexes), or rare earth complexes, and most preferred are iridium compounds.

In the present invention, at least one light emitting layer may contain two or more phosphorescent compounds. The concentration of these phosphorescent compounds in the light emitting layer may vary along the thickness direction of the light emitting layer.

Examples of the phosphorescent compounds which can be used in the present invention are listed in the following documents.

Nature 395,151 (1998), Appl. Phys. Lett. 78, 1622(2001), Adv. Mater. 19, 739(2007), Chem. Mater. 17, 3532(2005), Adv. Mater. 17, 1059(2005), International Publication Nos. 2009/100991, 2008/101842, and 2003/040257, and United States Patent Application Nos. 2006/835469, 2006/0202194, 2007/0087321, and 2005/0244673.

Further examples include Inorg. Chem. 40, 1704(2001), Chem. Mater. 16, 2480(2004), Adv. Mater. 16, 2003(2004), Angew. Chem. Int. Ed. 2006, 45, 7800, Appl. Phys. Lett. 86, 153505(2005), Chem. Lett. 34, 592(2005), Chem. Commun. 2906 (2005), Inorg. Chem. 42, 1248(2003), International Publication Nos. 2009/050290 and 2009/000673, U.S. Pat. No. 7,332,232, United States Patent Application No. 2009/0039776, U.S. Pat. No. 6,687,266, United States Patent Application Nos. 2006/0008670 and 2008/0015355, U.S. Pat. No. 7,396,598, United States Patent Application No. 2003/0138657, and U.S. Pat. No. 7,090,928.

Further examples include Angew. Chem. Int. Ed. 47, 1 (2008), Chem. Mater. 18, 5119(2006), Inorg. Chem. 46, 4308(2007), Organometallics 23, 3745(2004), Appl. Phys. Lett. 74, 1361(1999), International Publication Nos. 2006/056418, 2005/123873, 2005/123873, and 2006/082742, United States Patent Application No. 2005/0260441, U.S. Pat. No. 7,534,505, United States Patent Application No. 2007/0190359, U.S. Pat. Nos. 7,338,722 and 7,279,704, and United States Patent Application No. 2006/103874.

Further examples include International Publication Nos. 2005/076380, 2008/140115, 011/134013, 2010/086089, 2012/020327, 2011/051404, and 2011/073149, and Japanese Unexamined Patent Application Publication Nos. 2009-114086, 2003-81988, and 2002-363552.

Preferred phosphorescent compounds in the present invention include organometallic complexes containing iridium (Ir) as a central atom. More preferred are complexes having at least one of the coordinate bond selected from a metal-carbon bond, a metal-nitrogen bond, a metal-oxygen bond, and a metal-sulfur bond.

Such phosphorescent compounds (also referred to as phosphorescent metal complexes) may be prepared by the processes described, for example, in the following documents and references cited in these documents: Organic Letter, vol. 3, No. 16, pp. 2579-2581 (2001), Inorganic Chemistry, vol. 30, No. 8, pp. 1685-1687 (1991), J. Am. Chem. Soc., vol. 123, p. 4304 (2001), Inorganic Chemistry, vol. 40, No. 7, pp. 1704-1711 (2001), Inorganic Chemistry, vol. 41, No. 12, pp. 3055-3066 (2002), New Journal of Chemistry., vol. 26, P. 1171 (2002), and European Journal of Organic Chemistry, vol. 4, pp. 695-709 (2004).

<Fluorescent Compound>

The fluorescent compound include coumarin dyes, pyran dyes, cyanine dyes, croconium dyes, squarylium dyes, oxobenzanthracene dyes, fluorescein dyes, rhodamine dyes, pyrylium dyes, perylene dyes, stilbene dyes, polythiophene dyes, and rare earth complex phosphors.

(Carrier Transporting Functional Layer Group)

Next, typical example of individual layers constituting the carrier transporting functional layer group, the charge injecting layer, the hole transporting layer, the electron transporting layer, and a blocking layer, will now be described in sequence.

(Charge Injecting Layer)

The charge injecting layer is a layer provided between the electrode and the light emitting layer, so that the driving voltage is reduced and the emission luminance is improved. The detail of the charge injecting layer is described in "Yuuki EL Soshi to sono Kogyoka Saizensen (Front Line in Industrialization of Organic EL element)", Part II, Chapter 2, pp. 123-166, "Denkyoku Zairyo (Electrode materials)" (Nov. 30, 1998 by N. T. S. Company). The charge injecting layer is classified into a hole injecting layer and an electron injecting layer.

Among the charge injecting layer, the hole injecting layer is usually arranged between the anode and the light emitting layer or the hole transporting layer, while the electron injecting layer is usually arranged between the cathode and the light emitting layer or the electron transporting layer. The present invention is characterized in that the charge injecting layer is arranged adjacent to an electrode having light transmittance. In the case where the charge injecting layer is used as an intermediate electrode, at least one of the adjacent electron injecting layer and the hole injecting layer is required to satisfy the requirement of the present invention.

The hole injecting layer is a layer provided adjacent to the anode which is a light-transmitting electrode, so that the driving voltage is reduced and the emission luminance is improved. The detail of the charge injecting layer is described in "Yuuki EL Soshi to sono Kogyoka Saizensen (Front Line in Industrialization of Organic EL element)", Part II, Chapter 2, pp. 123-166, "Denkyoku Zairyo (Electrode materials)" (Nov. 30, 1998 by N. T. S. Company).

The hole injecting layer is also described in detail in Japanese Unexamined Patent Application Publication Nos. Hei 9-45479, Hei 9-260062, and Hei 8-288069. Examples of materials for the hole injecting layer include porphyrin derivatives, phthalocyanine derivatives, oxazole derivatives, oxadiazole derivatives, triazole derivatives, imidazole derivatives, pyrazoline derivatives, pyrazolone derivatives, phenylenediamine derivatives, hydrazone derivatives, stilbene derivatives, polyarylalkane derivatives, triarylamine derivatives, carbazole derivatives, indrocarbazole derivatives, isoindole derivatives, acene derivatives such as anthracene and naphthalene, fluorene derivatives, fluorenone derivatives, polyvinylcarbazole, high molecular weight materials or oligomers having aromatic amine main or side chains, polysilanes, and conductive polymers or oligomers (for example, polyethylene dioxythiophene (PEDOT)/polystyrene sulfonate (PSS), aniline copolymers, polyaniline, and polythiophene).

Examples of the triarylamine derivatives include benzidine types such as α-NPD (4,4'-bis(N-(1-naphthyl)-N-phenylamino)biphenyl), star-burst types such as MTDATA (4,4', 4"-tris(N-(3-methylphenyl)-N-phenylamino) triphenylamine), and compounds having fluorene and anthracene in the triarylamine coupling cores.

Alternatively, the hole transporting material may be hexaazatriphenylene derivatives described in Japanese translation of PCT application 2003-519432 and Japanese Unexamined Patent Application Publication No. 2006-135145.

The electron injecting layer is a layer provided between the cathode and the light emitting layer, so that the driving voltage is reduced and the emission luminance is improved. In the case where the cathode includes an electrode having light transmittance according to the present invention, the electron injecting layer is provided adjacent to the electrode having light transmittance. The detail of the electron injecting layer is described in "Yuuki EL Soshi to sono Kogyoka Saizensen (Front Line in Industrialization of Organic EL element)", Part II, Chapter 2, pp. 123-166, "Denkyoku Zairyo (Electrode materials)" (Nov. 30, 1998 by N. T. S. Company).

The electron injecting layer is also described in detail, for example, in Japanese Unexamined Patent Application Publication Nos. Hei 6-325871, Hei 9-17574, and Hei 10-74586. Examples of preferred materials for the electron injecting layer include metals such as strontium and aluminum; alkali metal compounds such as lithium fluoride, sodium fluoride, and potassium fluoride; alkali metal halides such as magnesium fluoride and calcium fluoride; alkaline earth metal compounds such as magnesium fluoride; metal oxides such as molybdenum oxide and aluminum oxide; and metal complexes such as lithium-8-hydroxyquinolate (Liq). In the case where the cathode is an electrode having light transmittance according to the present invention, organic materials such as metal complexes are particularly preferred. Preferably, the electron injecting layer should have a significantly small thickness within the range of 1 nm to 10 µm, although it depends on the materials constituting the layer.

(Hole Transporting Layer)

The hole transporting layer is composed of a hole transporting material, which has a function of transporting holes. The hole injecting layer and the electron blocking layer also function as a hole transporting layer in a broad sense. The hole transporting layer may have a monolayer or multilayer structure.

The hole transporting material inject holes, transport holes, or block electrons and may be either organic or inorganic compound. Examples of such materials include triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline copolymers, conductive high molecular weight oligomers, and thiophene oligomers.

The hole transporting material may be porphyrin compounds, tertiary aromatic amine compounds, and styrylamine compounds, besides the compounds described above. Preferred are tertiary aromatic amine compounds, in particular.

Typical examples of the tertiary aromatic amine compounds and styrylamine compounds include N,N,N',N'-tetraphenyl-4,4'-diaminophenyl, N,N'-diphenyl-N,N'-bis(3-methylphenyl)-[1,1'-biphenyl]-4,4'-diamine (abbreviation: TPD), 2,2-bis(4-di-p-tolylaminophenyl)propane, 1,1-bis(4-di-p-tolylaminophenyl)cyclohexane, N,N,N',N'-tetra-p-tolyl-4,4'-diaminobiphenyl, 1,1-bis(4-di-p-tolylaminophenyl)-4-phenylcyclohexane, bis(4-dimethylamino-2-methylphenyl)phenylmethane, bis(4-di-p-tolylaminopnenyl)phenylmethane, N,N'-diphenyl-N,N'-di (4-methoxyphenyl)-4,4'-diaminobiphenyl, N,N,N',N'-tetraphenyl-4,4'-diaminodiphenyl ether, 4,4'-bis(diphenylamino)quodriphenyl, N,N,N-tri(p-tolyl)amine, 4-(di-p-tolylamino)-4'-[4-(di-p-tolylamino)styryl]stilbene, 4-N,N-diphenylamino-(2-diphenylvinyl)benzene, 3-methoxy-4'-N,N-diphenylaminostyrylbenzene, and N-phenylcarbazole.

A thin film of the hole transporting layer can be formed with the above-described hole transporting material by any known method, for example, a vacuum evaporation method, a spin coating method, a casting method, a printing method such as an ink jetting method, or Langmuir Blodgett (LB) method. The hole transporting layer may have any thickness, usually a thickness in the range of about 5 nm to 5 µm, preferably 5 to 200 nm. The hole transporting layer may have a single layer structure composed of one kind or two or more kinds of the materials described above.

The p characteristics can be enhanced by doping the materials of hole transporting layer with any impurity. Examples are described in Japanese Unexamined Patent Application Publication Nos. Hei 4-297076, 2000-196140, and 2001-102175, and J. Appl. Phys., 95, 5773(2004).

A hole transporting layer with enhanced p characteristics is preferred because elements with low power consumption can be produced.

(Electron Transporting Layer)

The electron transporting layer includes a material which has a function of transporting electrons. The electron transporting layer also includes an electron injecting layer and a hole blocking layer in a broad sense. The electron transporting layer may have a monolayer or multilayer structure.

In an electron transporting layer having a monolayer structure and an electron transporting layer having a multilayer structure, the electron transporting material (also functioning as hole blocking material) constituting a layer adjacent to the light emitting layer is required only to have a function of transporting electrons injected from the cathode to the light emitting layer. Such materials can be selected from any conventionally known materials and can be used. Examples of such materials include nitro-substituted fluorene derivatives, diphenylquinone derivatives, thiopyrane dioxide derivatives, carbodiimides, fluorenylidene methane derivatives, anthraquinodimethane, anthrone derivatives, and oxadiazole derivatives. In addition, thiadiazole derivatives in which the oxygen atom in the oxadiazole ring is replaced with a sulfur atom in the above oxadiazole derivatives, and quinoxaline derivatives having quinoxaline rings, which are known as electron attractive groups, may also be used as materials for the electron transporting layer. High molecular weight materials having these materials introduced in the macromolecular chain or having these materials as main chains may also be used.

Furthermore, materials for the electron transporting layer may be metal complexes of 8-quinolinol derivatives such as tris(8-quinolinol)aluminum (abbreviation: Alq$_3$), tris(5,7-dichloro-8-quinolinol)aluminum, tris(5,7-dibromo-8-quinolinol)aluminum, tris(2-methyl-8-quinolinol)aluminum, tris(5-metal-8-quinolinol)aluminum, and bis(8-quinolinol)zinc (abbreviation: Znq); and metal complexes of which the central metals are replaced with In, Mg, Cu, Ca, Sn, Ga, or Pb.

A thin film of the electron transporting layer can be formed with the electron transporting material by any known method, for example, a vacuum evaporation method, a spin coating method, a casting method, a printing method such as an ink jetting method, or Langmuir Blodgett (LB) method. The electron transporting layer may have any thickness, usually a thickness in the range of about 5 nm to 5 µm, preferably 5 to 200 nm. The electron transporting layer may have a single layer structure composed of one kind or two or more kinds of the materials described above.

(Blocking Layer)

The blocking layers include hole blocking layers and electron blocking layers. These layers may be provided as needed in addition to the individual layers constituting the carrier transporting functional layer unit 3 described above. Examples of the blocking layer are disclosed in Japanese Unexamined Patent Application Publication Nos. Hei 11-204258 and Hei 11-204359, and hole blocking layers described in "Yuuki EL Soshi to sono Kogyoka Saizensen (Front Line in Industrialization of Organic EL element)", p. 237, (Nov. 30, 1998 by N. T. S. Company).

The hole blocking layer also functions as an electron transporting layer in a broad sense. The hole blocking layer is composed of a hole blocking material which has a function of transporting electrons but can barely transport holes. Since the hole blocking layer transports electrons while blocking holes, the layer will enhance the opportunity of recombination of electrons and holes. The structure of the electron transporting layer may be used as a hole blocking layer as needed. Preferably, the hole blocking layer is arranged adjacent to the light emitting layer.

The electron blocking layer also functions as a hole transporting layer in a broad sense. The electron blocking layer is composed of a material which has a function of transporting holes but can barely transport electrons. Since the electron blocking layer transports holes while blocking electrons, the layer will enhance the opportunity of recombination of electrons and holes. The structure of the hole transporting layer may be used as an electron blocking layer. The hole blocking layer applied in the present invention preferably has a thickness in the range of 3 to 100 nm, more preferably in the range of 5 to 30 nm.

[Second Electrode: Cathode]

The cathode according to the present invention is an electrode which has a light transmittance and a function of supplying holes to the carrier transporting functional layer group and the light emitting layer. The cathode includes a metal, alloy, organic or inorganic conductive compound, or a mixture thereof. Specific examples include gold, aluminum, silver, magnesium, lithium, magnesium/copper mixtures, magnesium/silver mixtures, magnesium/aluminum mixtures, magnesium/indium mixtures, indium, lithium/aluminum mixtures, rare earth metals, and oxide semiconductors such as ITO, ZnO, $TiO_2$, and $SnO_2$.

The cathode can be prepared by forming a thin film of these conductive materials by evaporation or sputtering. The cathode as a second electrode has a sheet resistance of preferably several hundred Ω/sq. or less, and the thickness selected in the range of generally 5 nm to 5 μm, preferably in the range of 5 to 200 nm.

[Other Components]

<Gas Barrier Layer>

At the entire surface of one side or both sides of the transparent substrate (1), at least the side where the anode (first electrode) is formed, a gas barrier layer (2) having light transmittance is formed so that permeation of components such as water and oxygen, which deteriorate the constituting materials of the organic EL element, can be suppressed.

The gas barrier layer (2) may be not only a coating film of an inorganic material, but a coating film composed of a composite material including an organic material or a hybrid coating material obtained by laminating such coating films. The gas barrier layer (2) is preferably an insulating film having light transmittance and a gas barrier property as follows: water vapor permeability of about 0.01 $g/m^2 \cdot 24$ h or less (environmental condition: 25±0.5° C., relative humidity (90±2)%) based on JIS (Japan Industrial Standards)-K7129 (2008); oxygen permeability of about 0.01 $ml/m^2 \cdot 24$ h·atm or less based on JIS-K7126 (2006); resistivity of $1\times10^{12}$ Ω·cm or more; and light transmission rate in the range of visible light of 80% or more.

Any materials can be used as the material for forming the gas barrier layer (2), as long as the material can suppress permeation of, for example, water and gas such as oxygen into the organic El element, which deteriorates the organic EL element.

The gas barrier layer (2) may include a coating film composed of an inorganic material such as silicon oxide, silicon nitride, silicon oxynitride, silicon carbide, silicon oxycarbide, aluminium oxide, aluminium nitride, titanium oxide, zirconium oxide, niobium oxide, and molybdenum oxide, for example. Preferably, silicon compounds such as silicon nitride and silicon oxide is used as a main raw material.

The formation method of the gas barrier layer can be appropriately selected from conventionally known methods of producing films, such as a vacuum evaporation method, a sputtering method, a magnetron sputtering method, a molecular beam epitaxy method, a cluster ion beam method, an ion plating method, a plasma polymerization method, an atmospheric-pressure plasma polymerization method (see Japanese Patent Application Laid Open Publication No. 2004-68143), a plasma CVD (Chemical Vapor Deposition) method, a laser CVD method, thermal CVD method, ALD (Atomic Layer Deposition) method, and a wet application method using polysilazane and the like.

<Sealing Material>

The exemplary organic EL panel (P) in FIG. 2 shows an organic EL panel (P) provided with an organic EL element (OLED) formed up to the cathode (7), further provided with a sealing member formed above.

As shown in FIG. 2, the entire surface of the organic EL element (OLED) is provided with a sealing adhesive (8) and sealed with the sealing substrate (10) having the gas barrier layer (9) on the outermost surface.

The sealing member may have a concave shape or a flat shape, as long as the sealing member is arranged so that the display region of the organic EL element is covered. The transparency and the electrical insulating property are not particularly limited.

Specific examples include a glass substrate, a resin substrate, resin film, metal film (metal foil), and the like having flexibility. Examples of the glass substrate include, in particular, soda lime glass, barium and strontium containing glass, lead glass, aluminosilicate glass, borosilicate glass, barium borosilicate glass, quartz, and the like. Examples of the resin substrate include polycarbonate, acrylic, poly(ethylene terephthalate), polyether sulfide, polysulfone, and the like.

Examples of the sealing adhesive include polyurethane adhesives, polyester adhesives, epoxy adhesives, and acrylic adhesives. A curing agent may be optionally used in combination as needed. A dry lamination method is preferred, but a hot-melt lamination method, an extrusion lamination method, or a co-extrusion lamination method may also be used.

Resin substrate and glass substrate can be preferably used as the sealing material according to the present invention because the organic EL element can be thinned. Preferably, the resin substrate has water vapor permeability of $1\times10^{-3}$ $g/m^2 \cdot 24$ h or less which is measured in accordance with JIS K 7129-1992 at the temperature of 25±0.5° C. and relative humidity of 90±2% RH. More preferably, the resin substrate has oxygen permeability of $1\times10^{-3}$ $ml/m^2 \cdot 24$ h·atm (1 atm corresponds to $1.01325\times10^5$ Pa) which is measured in accordance with JIS K 7126-1987, and water vapor permeability of $1 \times 10^{-3}$ g/m$^2$·24 h or less at the temperature of 25±0.5° C. and relative humidity of 90±2% RH. In order to satisfy the conditions, a gas barrier layer is preferably provided, which is equivalent to the one explained for the base material described above.

At the gap between the sealing member and the display region (light emitting region) of the organic EL element can be injected inactive gas such as nitrogen gas and argon gas, or an inactive liquid such as silicon oil, for the purpose of forming a gaseous or a liquid phase. The gap between the sealing member and the display region of the organic EL element may be vacuum. Alternatively, the gap may be filled with a hygroscopic compound.

The sealing film may be provided on the substrate having light transmittance, while completely covering the organic functional layer unit of the organic EL element and exposing the terminals of the anode (3) as the first electrode and the cathode (7) as the second electrode of the organic EL element.

<<Specific Structure of the Organic EL Panel>>

Subsequently, the specific structure of the organic EL panel according to the present invention is described.

The organic EL panel according to the present invention includes a light emitting portion region which is shaped by the organic electroluminescence element and a light-transmitting non-light emitting portion region.

Hereinafter, the specific structure of the organic EL panel including the light emitting portion region (light emitting area) and non-light emitting portion is explained.

Embodiment 1: Formation Method 1 of Organic EL Panel

FIG. 3 is a schematic cross-sectional view showing an exemplary structure of the organic EL panel (P) according to the invention having an organic EL element (Embodiment 1).

The organic EL panel (P) illustrated in FIG. 3 has independent light emission areas shaped by arranging organic EL panels separate from each other on a transparent base material (1) having light transmittance in the organic EL element described in reference to FIG. 2 above. For more details, on the transparent base material (1) having the gas barrier layer (2) are arranged a plurality of organic EL elements (OLEDs) constituted by, for example, the anodes (3), the organic functional layer units (U), the cathodes (7), and so forth.

According to the structure illustrated in FIG. 3, the light emitting areas are regions in which all of the anode (3), the organic functional layer unit (U), and the cathode (7) exist. A region between the light emitting areas is the light-transmitting non-light emitting area (12). In the structure illustrated in FIG. 3, a finger at the lower surface side is irradiated with light (L1) from the finger surface side having the anodes (3). The image sensor (S) is arranged at the upper surface side of the light-transmitting non-light emitting portion (12).

In the structure illustrated in FIG. 3, most preferably, the anodes (3) are constituted by light-transmitting electrodes and the cathodes (7) are constituted by non-light emitting electrodes, however, both of the anodes (3) and the cathodes (7) may be constituted by light-transmitting transparent electrodes.

Embodiment 2: Formation Method 2 of Organic EL Panel

The organic EL panel (P) having a structure illustrated in FIG. 4 shows another exemplary structure in which the cathodes (7) are constituted by non-light transmitting electrodes, in particular, in the structure explained above in reference to FIG. 3. Such structure prevents irradiation of the image sensor side with irregular light which affects the measurement accuracy of the image sensor from the cathode (7) side of the organic EL element. Accordingly, the image sensor (S) can be arranged on the entire surface including the light emitting area.

Embodiment 3: Formation Method 3 of Organic EL Panel

Figure 5:
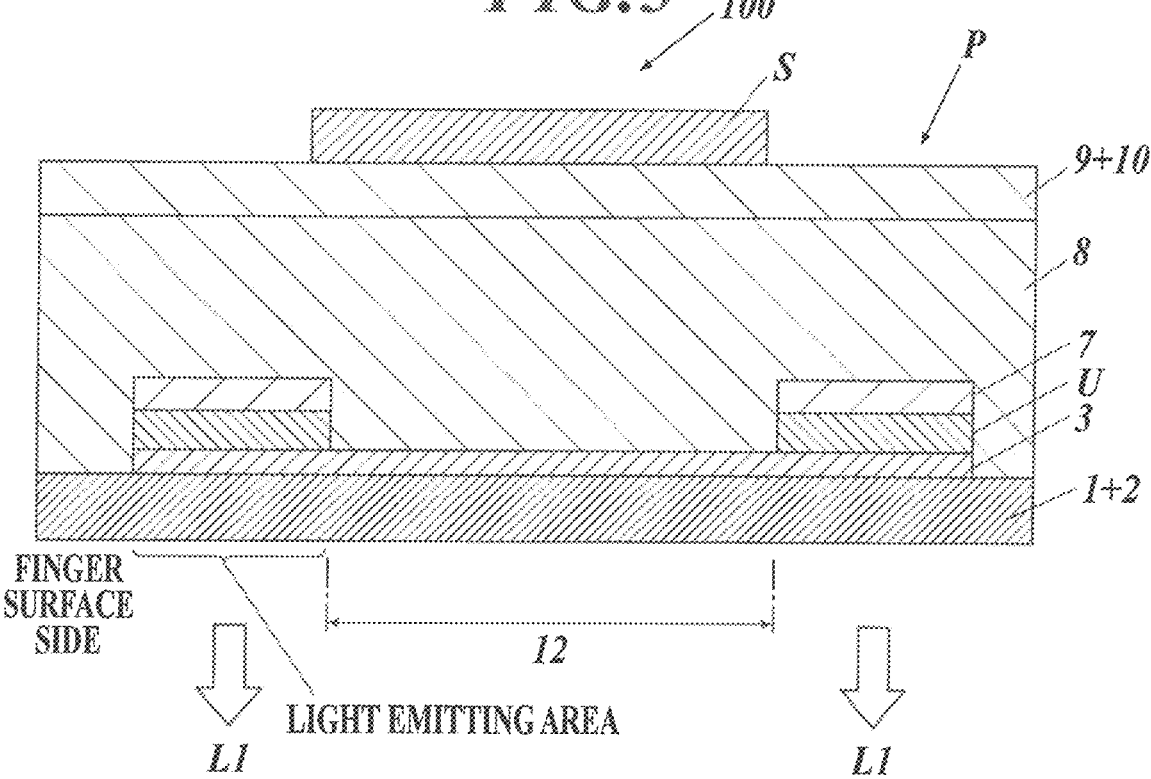
FIG. 5 is a schematic cross-sectional view showing another exemplary structure of an organic EL panel which can be applied to the present invention (Embodiment 3).

The organic EL panel (P) having the structure illustrated in FIG. 5 shows a method of forming the organic EL element in which the light-transmitting anode (3) is formed at the entire surface of the light emitting area and the non-light emitting portion (12), so that only the organic functional layer units (U) and the cathodes (7) shape the light emitting area.

The light emitting area is required to have a structure in which all of the anode (3), the organic functional layer units (U), and the cathodes (7) are present in a single plane. As illustrated in FIG. 5, the region in which only the anode (3) is present functions as the non-light emitting portion (12).

Embodiment 4: Formation Method 4 of Organic EL Panel

Figure 6:
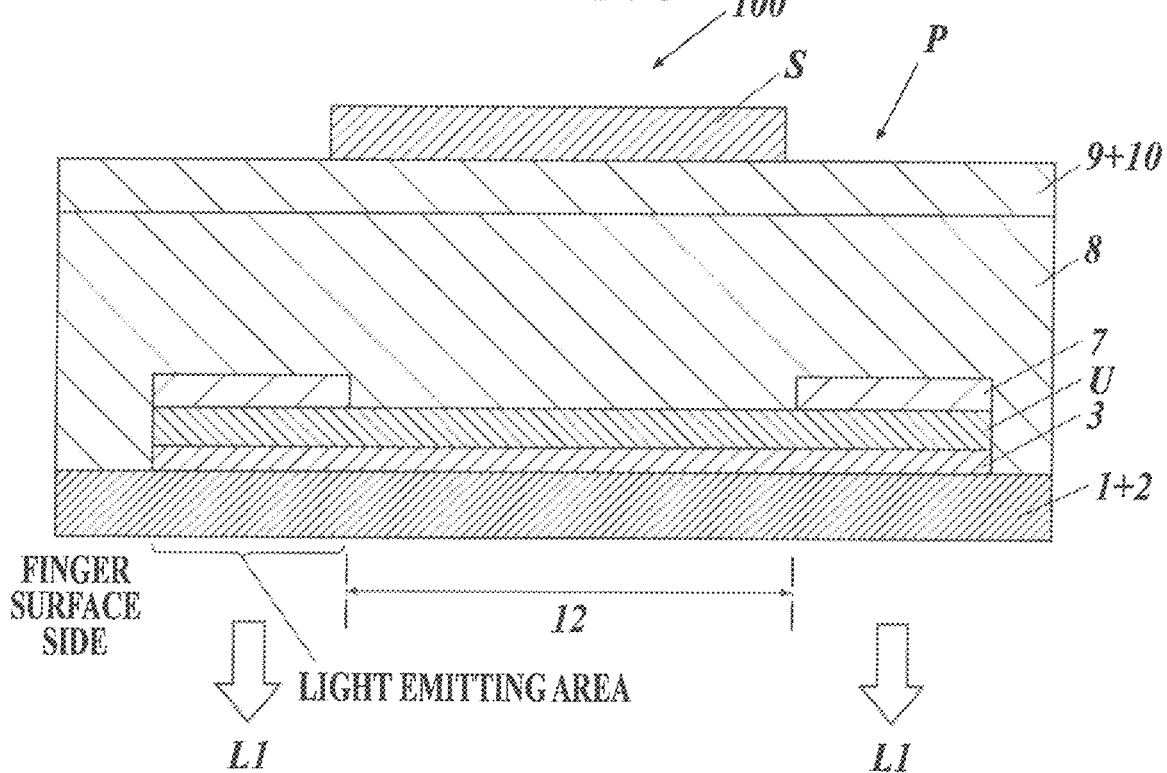
FIG. 6 is a schematic cross-sectional view showing another exemplary structure of an organic EL panel which can be applied to the present invention (Embodiment 4).

The organic EL panel (P) having the structure illustrated in FIG. 6 shows a method of forming the organic EL element in which the anode (3) and the organic functional layer unit (U) are formed at the entire surface of the light emitting area and the non-light emitting portion (12), so that only the cathodes (7) shape the light emitting area.

The light emitting area is required to have a structure in which all of the anode (3), the organic functional layer unit (U), and the cathodes (7) are present in a single plane. As illustrated in FIG. 6, the region in which the cathodes (7) are not present functions as the non-light emitting portion (12).

Embodiment 5: Formation Method 5 of Organic EL Panel

Figure 7:
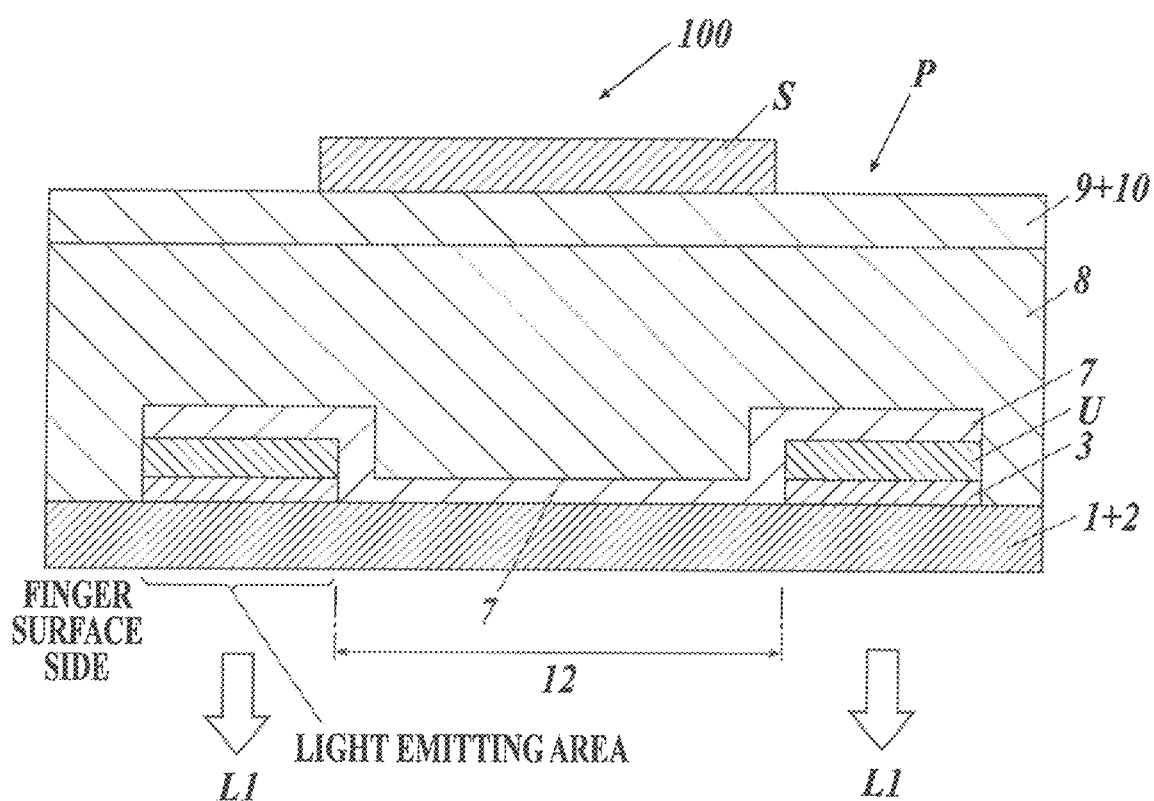
FIG. 7 is a schematic cross-sectional view showing another exemplary structure of an organic EL panel which can be applied to the present invention (Embodiment 5).

The organic EL panel (P) having the structure illustrated in FIG. 7 shows a method of forming the organic EL element in which the anodes (3) and the organic functional layer unites (U) are formed only at the light emitting area as illustrated in FIG. 4. The cathode (7) preferably has light transmittance since the cathode (7) is also present at the non-light emitting portion (12).

The light emitting area is required to have a structure that all of the anodes (3), the organic functional layer units (U), and the cathode (7) are present in a single plane. As shown in FIG. 7, the region in which the anodes (3) and the organic functional layer units (U) are not present functions as the non-light emitting portion (12).

Embodiment 6: Formation Method 6 of Organic EL Panel

The formation method of the organic EL panel (P) illustrated in FIG. 8 can be a method of forming the non-light emitting portion (U2) in the organic functional layer unit by forming the anode (3), organic functional layer unit (U), and the cathode (7) on the entire surface of the transparent substrate (1+2), followed by irradiating the region for forming the non-light emitting portion (12) with ultraviolet rays (UV) by an ultraviolet-ray irradiating apparatus (13) through a mask member (M) so that the light emitting function of the organic functional layer unit is deactivated.

The method is not particularly limited, and may be either a method of light irradiation after forming the organic functional layer unit (U) or a method of patterning the light emitting area by irradiating the organic EL panel (P) with light after sealing process. The latter method is preferred because the organic EL panel after sealing can be subjected to light irradiation during exposure to an air atmosphere, which realizes an easy light irradiation step and low manufacturing costs.

Figure 8A:
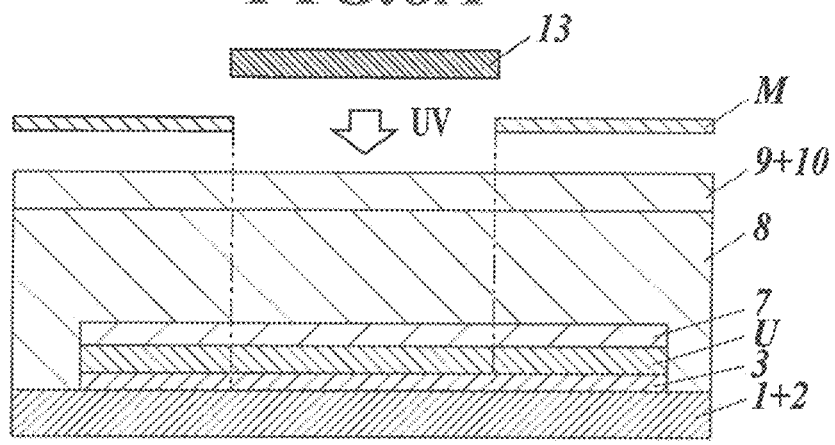
FIG. 8A is a schematic cross-sectional view showing the first step of a formation method of an organic EL panel which can be applied to the present invention (Embodiment 6).
Figure 8B:
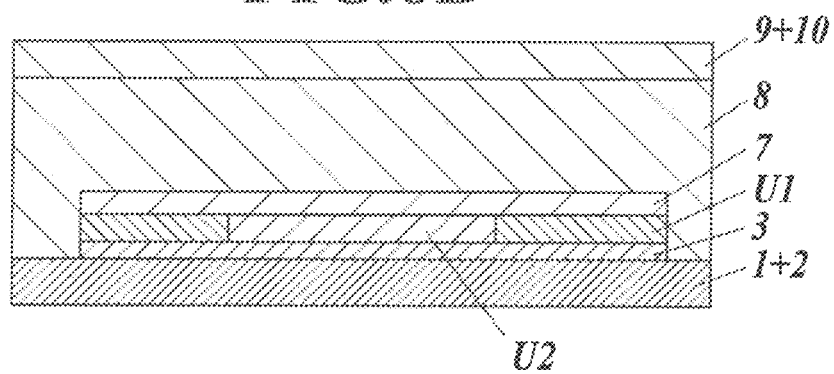
FIG. 8B is a schematic cross-sectional view showing the second step of a formation method of an organic EL panel which can be applied to the present invention (Embodiment 6).

As the first step, as illustrated in FIG. 8A, the organic EL element is formed by the sealing process after forming an anode (3), organic functional layer unit (U), and the cathode (7) on the entire surface of the transparent substrate (1).

Subsequently, irradiation with ultraviolet rays (UV) by the ultraviolet-ray irradiating apparatus (13) is performed after shielding the region except for the region of the non-light emitting portion (12) with the mask member (M)

By the irradiation process with the ultraviolet rays described above, as illustrated in FIG. 8B showing the second step, the function of the organic functional layer unit (U1) is deactivated in the region irradiated with the ultraviolet rays (UV) so that the non-light emitting portion (U2) is shaped.

Figure 8C:
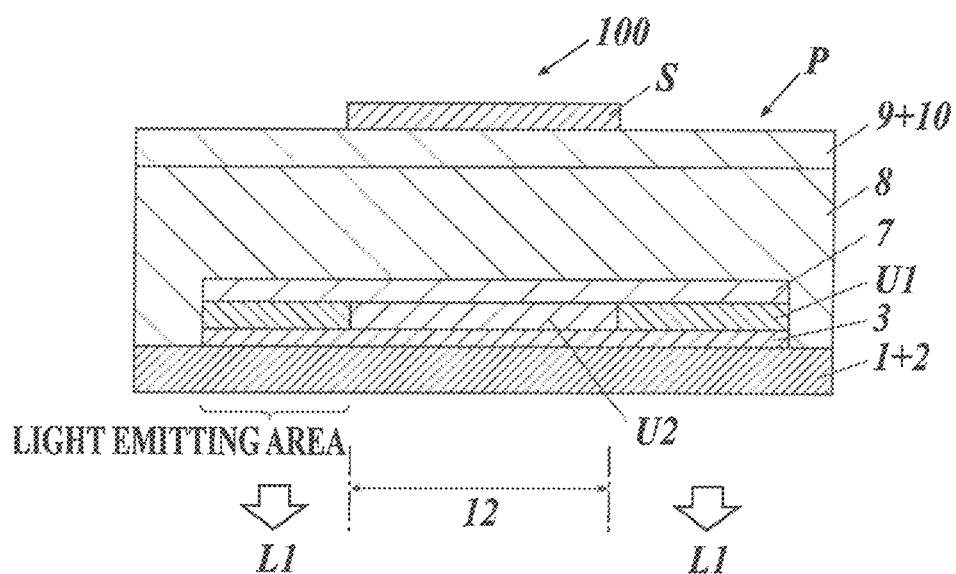
FIG. 8C is a schematic cross-sectional view showing the third step of a formation method of an organic EL panel which can be applied to the present invention (Embodiment 6).

Subsequently, as illustrated in FIG. 8C showing the third step, the image sensor (S) is arranged above the non-light emitting portion (12, U2) to manufacture the fingerprint information reader (100).

In the formation method of the Embodiment 6, both of the anode (3) and the cathode (7) are required to be formed by a transparent electrode because the anode (3) and the cathode (7) are present in the area of the non-light emitting portion (12).

In the first step illustrated in FIG. 8A, which is the light irradiation step for pattern forming, the light for irradiation includes at least ultraviolet rays (UV) and may further include visible light or infrared rays. The ultraviolet rays according to the present invention refer to electromagnetic waves having a wavelength longer than the wavelength of X rays and shorter than the minimum wavelength of visible rays, specifically, within the wavelength range within 1 to 400 nm. Preferably, the applied light for irradiation has local maximum wavelengths at 355 nm, 365 nm, 380 nm, 405 nm, and so forth.

The generation means and the irradiation means of the light for irradiation are not particularly limited, as long as a predetermined region can be irradiated with light which is generated by a conventionally known irradiation device.

The a light source for illumination which can be used in the present invention include a high-pressure mercury lamp, a low-pressure mercury lamp, a hydrogen (deuterium) lamp, a rare gas (such as xenon, argon, helium, and neon) discharge lamp, nitrogen laser, excimer laser (such as XeCl, XeF, KrF, and KrCl), hydrogen laser, halogen laser, harmonic waves of a visible (LD) laser to an infrared laser (THG (Third Harmonic Generation) light of YAG laser), and the like.

The method of laser light irradiation includes moving the laser light source and the organic functional layer unit (U) relative to each other while irradiating the organic functional layer unit (U) with the laser light in spot, so that the patterned region can be irradiated with light by scanning the laser light irradiation position.

<<Embodiment of Optical Fingerprint Authentication Device Provided with Fingerprint Information Reader>>

Next, with reference to the drawings will now be described specific structures of the fingerprint information reader constituting the optical fingerprint authentication device using the organic EL panel provided with the organic EL element according to the present invention.

Embodiment 7: Exemplary Configuration 1 of Fingerprint Information Reader

Figure 9:
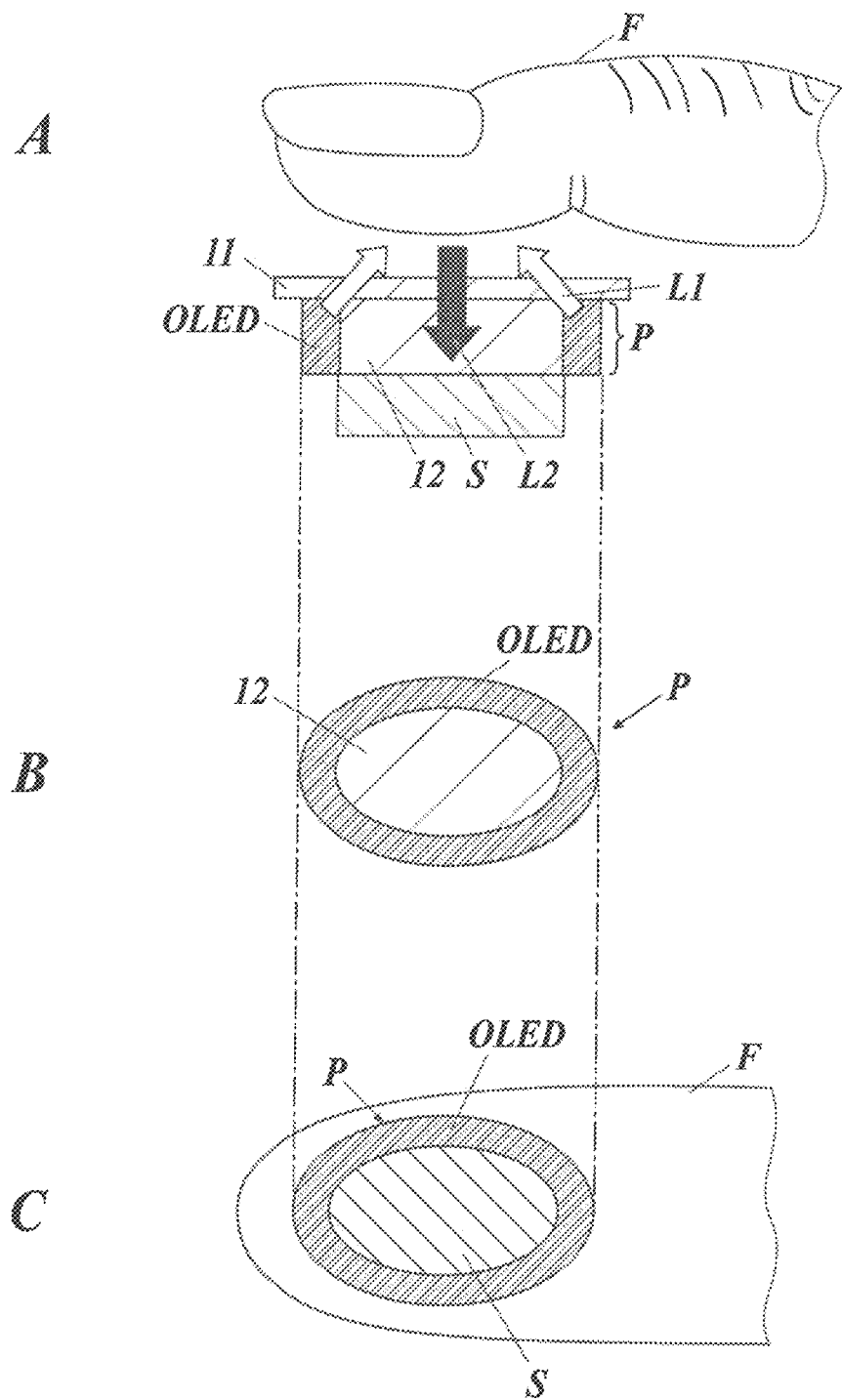
FIG. 9 is a schematic diagram showing an exemplary optical fingerprint authentication device provided with a fingerprint information reader having an organic EL panel provided with a doughnut-shaped organic EL element (Embodiment 7).

FIG. 9 is a schematic diagram showing an exemplary fingerprint information reader having an organic EL panel provided with a doughnut-shaped organic EL element (Embodiment 7).

The cross-sectional view illustrated in FIG. 9 shows a same structure as the fingerprint information reader (100) constituting the optical fingerprint authentication device previously described in reference to FIG. 1. There are provided an organic EL panel (P) which is constituted by the organic EL element (OLED) and a light-transmitting non-light emitting portion (12), and by the image sensor (S) which is arranged below the light-transmitting non-light emitting portion (12) and optically reads fingerprint information of a specimen. 11 is a glass substrate to hold the finger.

The fingerprint pattern information is obtained by irradiation of the fingerprint surface of the finger (F) with the irradiation light (L1) from the organic EL element (OLED) and receiving reflection light (L2), which is a light signal, by the image sensor (S).

The shape of the organic EL element (OLED) of the fingerprint information reader (100) having such structure may be, as illustrated in B of FIG. 9, a doughnut-shaped continuous organic EL element (OLED) arranged at the peripheral portion of the elliptic organic EL panel (P). The gap portion at the center is formed as the non-light emitting portion (12). Such embodiment of the organic EL element enables to measure the fingerprint pattern from a wide aperture.

C of FIG. 9 is a bottom view of the structure illustrated in A of FIG. 9 and shows the finger (F), which is the specimen, the doughnut-shaped organic EL element (OLED), and the image sensor (S) arranged at the non-light emitting region thereof. In C of FIG. 9, the glass substrate (11) is omitted.

Embodiment 8: Exemplary Configuration 2 of Optical Fingerprint Authentication Device FIG. 10 is a schematic diagram showing an exemplary optical fingerprint authentication device having an organic EL panel provided with a rectangular-shaped organic EL element (Embodiment 8).

Figure 10:
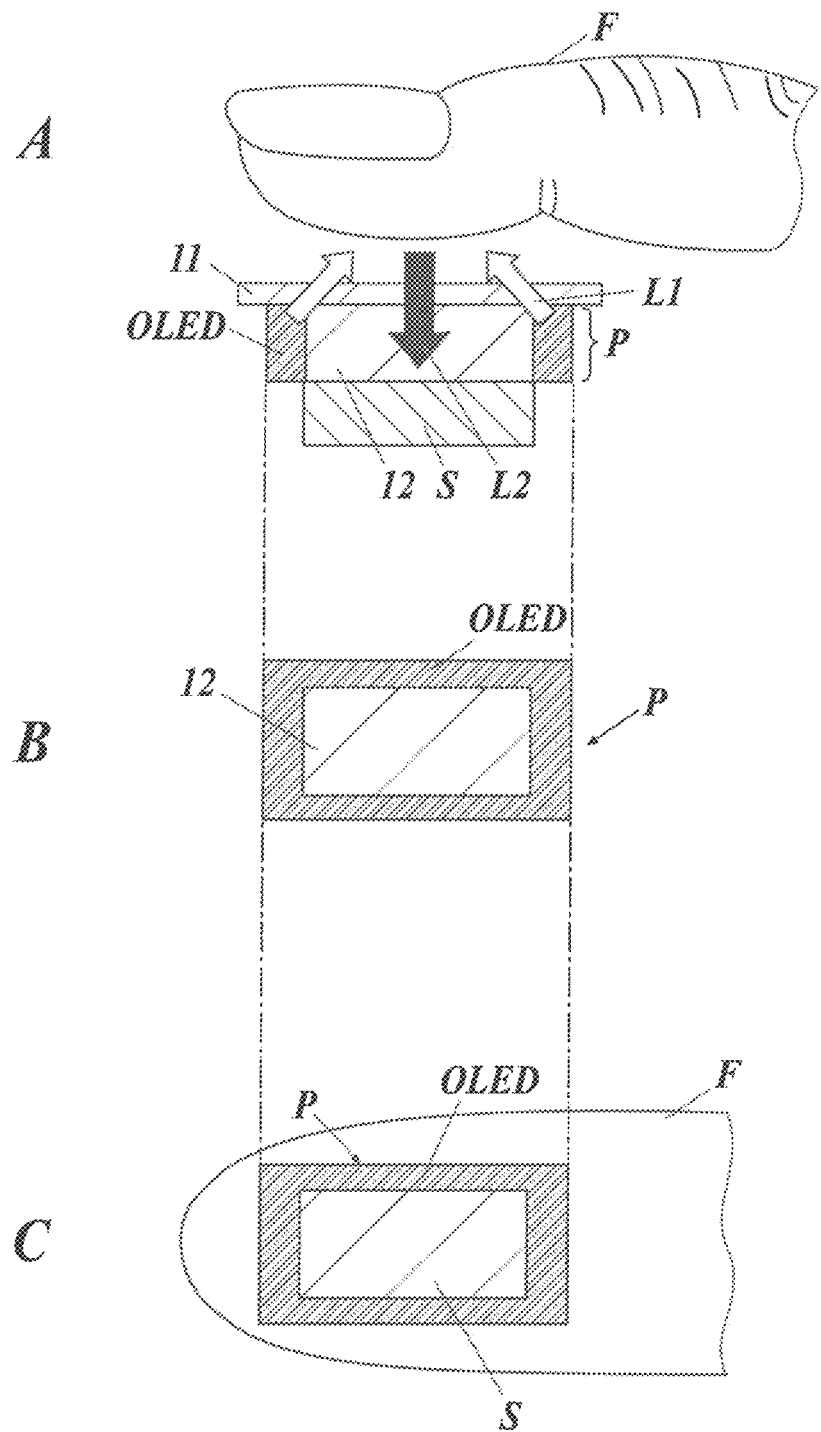
FIG. 10 is a schematic diagram showing an exemplary optical fingerprint authentication device provided with a fingerprint information reader having an organic EL panel provided with a rectangular-shaped organic EL element (Embodiment 8).

The schematic cross-sectional view illustrated in A of FIG. 10 is similar to that of the structure illustrated in A of FIG. 9 as described above, however, the organic EL panel (P) and the image sensor (S) is characterized by their rectangular shapes as illustrated in B and C of FIG. 10. The optical fingerprint authentication device having such structure, has difficulty in covering the entire fingerprint, which had a round shape, but provides an effective method for pattern detection of an important center portion of the fingerprint.

As illustrated in B of FIG. 10, the organic EL panel (P) has a rectangular shape having a continuous organic EL element (OLED) is arranged at the edges and the non-light emitting portion (12) also having a rectangular area formed inside, so that the image sensor (S) has a rectangular form corresponding to the form of the non-light emitting portion (12) as illustrated in C of FIG. 10. In C of FIG. 10, the glass substrate (11) is omitted.

On the organic EL panel (P) as illustrated in FIG. 9 and FIG. 10, the organic EL element (OLED) having a specific shape, such as a doughnut-shape or rectangular shape, can be formed by forming the anode (3), the organic functional layer unit (U), and the cathode (7) using a mask member of a desired shape by, for example, a vacuum evaporation method (such as a resistance heating deposition method, an electron beam deposition method, an ion plating method, and an ion beam evaporation method), a sputtering method, a reactive sputtering method, a molecular beam epitaxy method, a plasma polymerization method, an atmospheric-pressure plasma polymerization method, a plasma CVD method, a laser CVD method, a thermal CVD method, and wet application methods such as a screen printing method. Alternatively, as illustrated in FIG. 8, the function of the organic functional layer unit can be deactivated to form the organic EL element having a desired shape.

Embodiment 9: Exemplary Configuration 3 of Optical Fingerprint Authentication Device FIG. 11 is a schematic diagram showing an example of an optical fingerprint authentication device having an organic EL panel with strip-shaped organic EL elements arranged separately at four sides (Embodiment 9).

Figure 11:
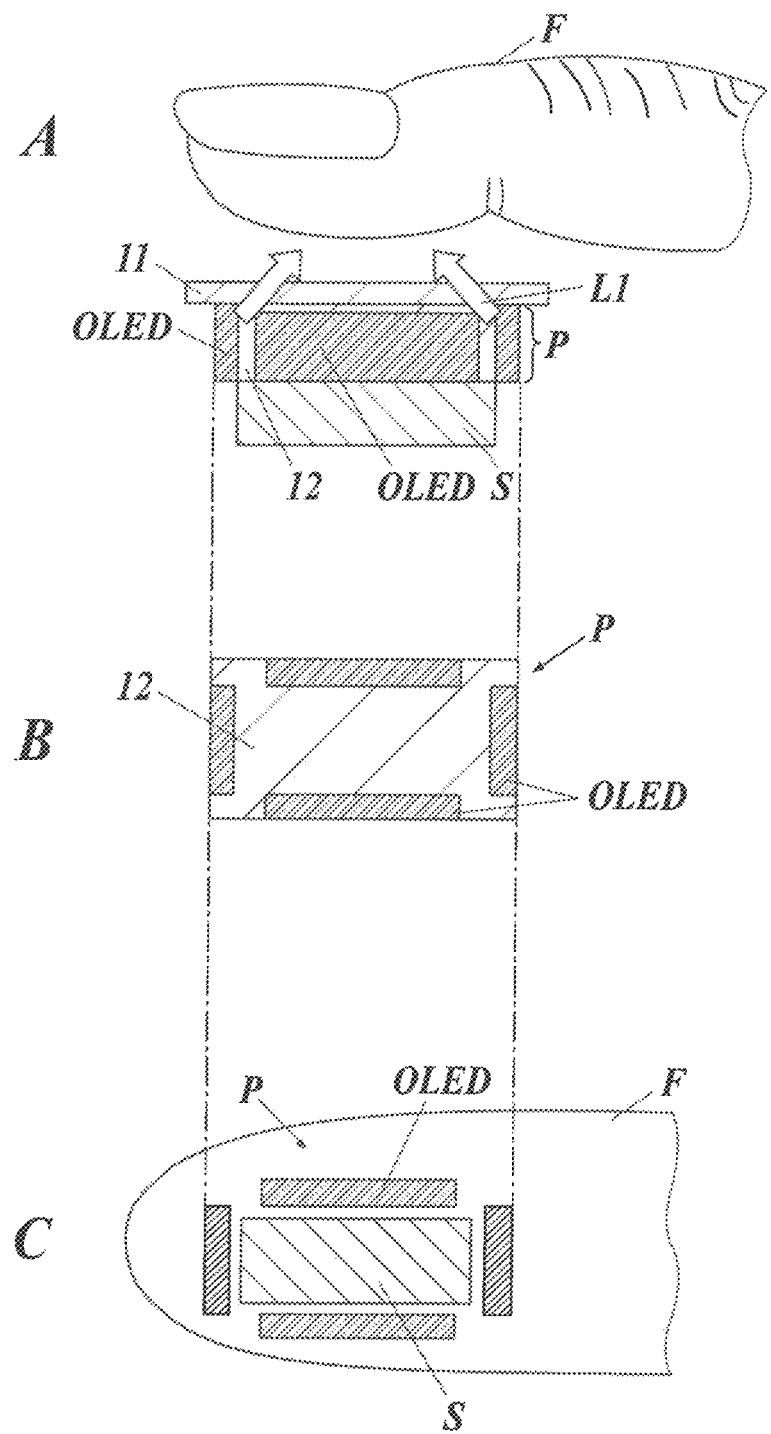
FIG. 11 is a schematic diagram showing an exemplary optical fingerprint authentication device provided with a fingerprint information reader having an organic EL panel provided with strip-shaped organic EL elements arranged at four sides (Embodiment 9).

The organic EL panel (P) according to the Embodiment 9 is constituted by, as illustrated in B of FIG. 11, independent and strip-shaped organic EL elements (OLEDs) arranged at each of the four sides of the rectangular organic EL panel (P). The non-light emitting portion (12) and the image sensor (S) have a rectangular shape. In C of FIG. 11, the glass substrate (11) is omitted.

Embodiment 10: Exemplary Configuration 4 of Optical Fingerprint Authentication Device FIG. 12 is a schematic diagram showing an exemplary optical fingerprint authentication device having a round-shaped organic EL panel having a rectangular-shaped non-light emitting portion at the center (Embodiment 10).

Figure 12:
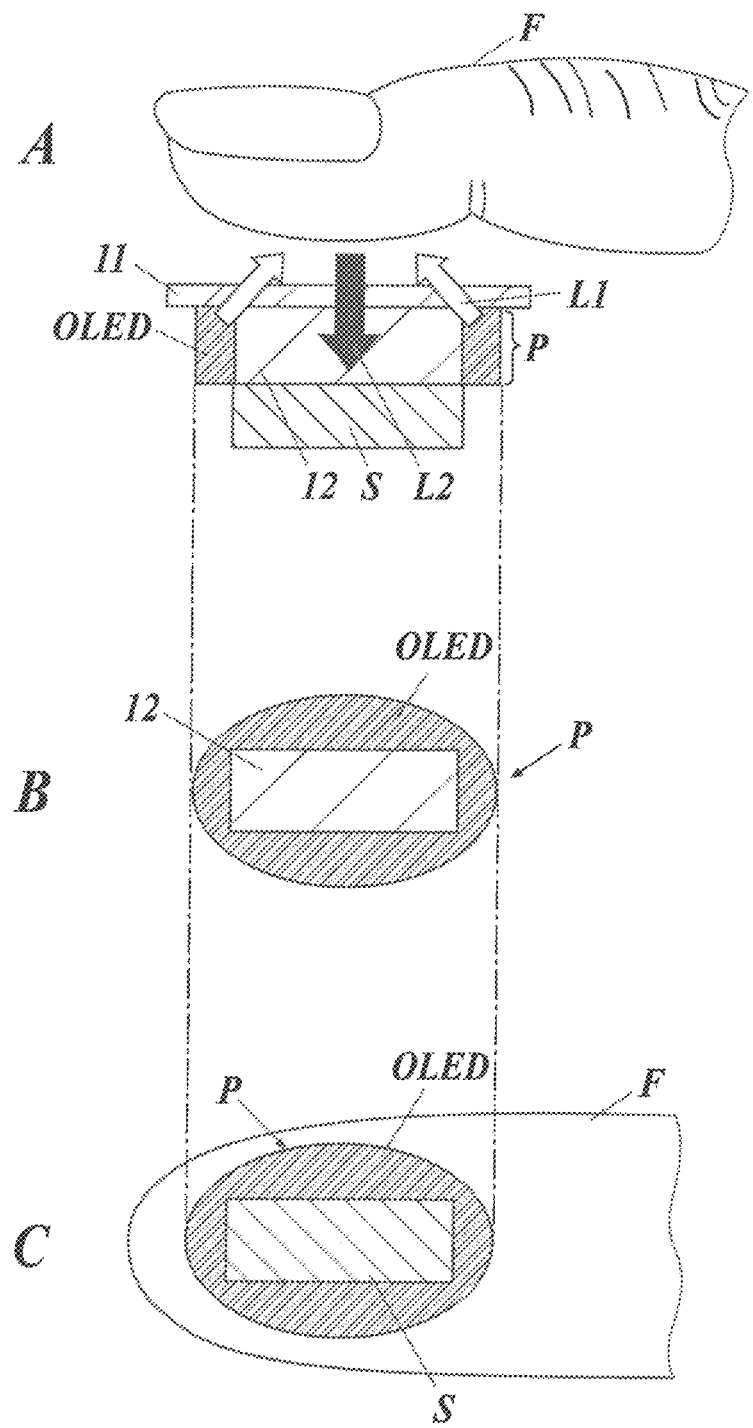
FIG. 12 is a schematic diagram showing an exemplary optical fingerprint authentication device provided with a fingerprint information reader having a round-shaped organic EL panel provided with a rectangular-shaped non-light emitting portion at the center (Embodiment 10).

As illustrated in B of FIG. 12, the peripheral portion of the organic EL panel (P) of the Embodiment 10 has a elliptic shape as in FIG. 9, and the non-light emitting portion (12) and the image sensor (S) arranged at the center portion have a rectangular shape. In C of FIG. 12, the glass substrate (11) is omitted.

Embodiment 11: Exemplary Configuration 5 of Optical Fingerprint Authentication Device FIG. 13 is a schematic diagram showing an exemplary optical fingerprint authentication device having an organic EL panel having a plurality of organic EL elements arranged in a stripe shape in parallel (Embodiment 11).

Figure 13:
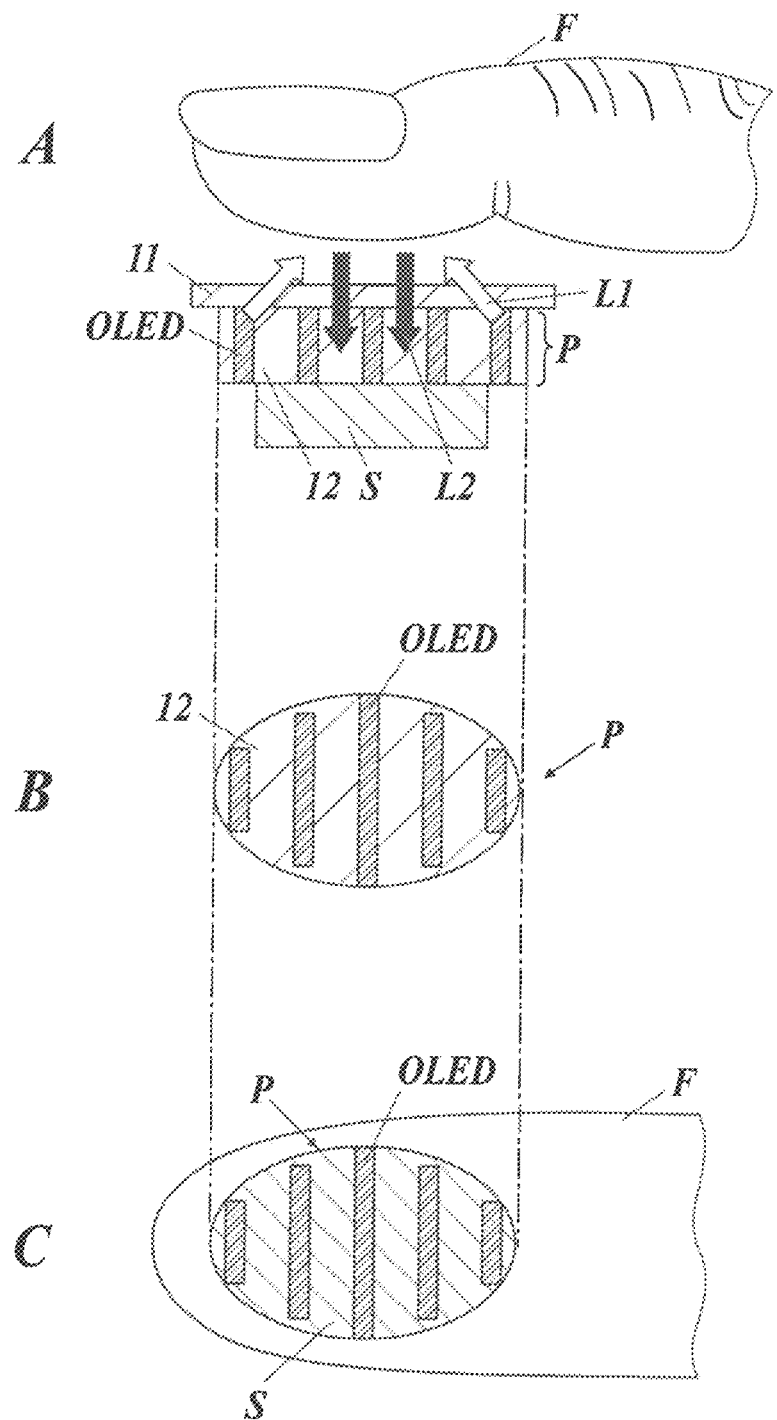
FIG. 13 is a schematic diagram showing an exemplary optical fingerprint authentication device provided with a fingerprint information reader having an organic EL panel provided with a plurality of strip-shaped organic EL elements arranged in a stripe shape in parallel (Embodiment 11).

According to the structure illustrated in B and C of FIG. 13, a plurality of organic EL elements (OLEDs) having different sizes are arranged in a stripe shape in parallel on the organic EL panel (P) of a elliptic shape. In C of FIG. 13, the glass substrate (11) is omitted.

In such a structure, the non-light emitting portion (12) is between the individual organic EL elements (OLEDs).

According to the structure illustrated in FIG. 13, the detectable area is narrow when the organic EL elements (OLEDs) occupy too large area. Therefore, the aperture rate (%) which is defined as the ratio of the area of the non-light emitting portion (12) to the entire area of the organic EL element (P) is preferably 50% or more, more preferably 60% or more, particularly preferably 70% or more. Because the total amount of light emission from the organic EL element (OLED) is reduced depending on the increase of the aperture rate, the organic EL element (OLED) having high emission intensity is preferably used. Examples of the organic EL element (OLED) having high emission intensity includes, for example, a tandem type organic EL element having two or more organic functional layer units including a light emitting layer via an intermediate layer or an intermediate electrode.

Embodiment 12: Exemplary Configuration 6 of Optical Fingerprint Authentication Device FIG. 14 is a schematic diagram showing an exemplary optical fingerprint authentication device having an organic EL panel with a plurality of organic EL elements arranged separately at the peripheral portion (Embodiment 12).

Figure 14:
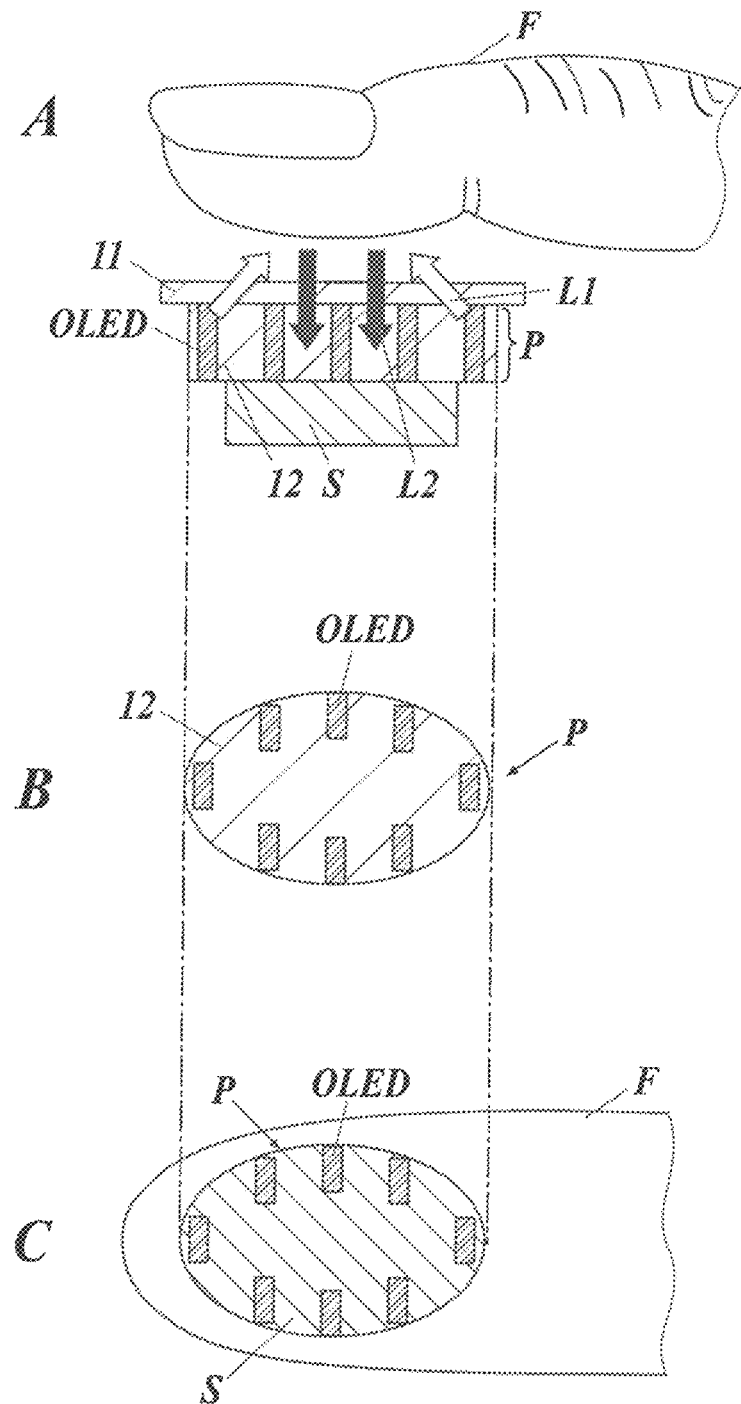
FIG. 14 is a schematic diagram showing an example of an optical fingerprint authentication device provided with an optical fingerprint information reader having an organic EL panel with a plurality of organic EL elements arranged separately at a peripheral portion (Embodiment 12).

As illustrated in B of FIG. 14, a plurality of rectangular organic EL elements (OLEDs) are arranged independently at the peripheral portion of the elliptic organic EL panel (P), and the non-light emitting portion (12) is formed between the organic EL elements (OLEDs) and at the center portion. In C of FIG. 14, the glass substrate (11) is omitted.

Such a structure is preferred in that a high aperture rate can be obtained in comparison with the structure of a stripe shape exemplified in FIG. 13.

<<Fingerprint Authentication Method>>

The specific fingerprint authentication method using the optical fingerprint authentication device according to the present invention can be appropriately selected for use from the methods described in, for example, Japanese Patent Application Laid Open Publication Nos. 2003-256377, 2004-005619, 2004-246586, 2005-063246, 2005-118289, 2006-244224, 2007-289457, 2007-328511, 2008-009821, 2008-171238, 2009-271825, 2011-141880, and the like.

Although embodiments of the present invention have been described and illustrated in detail, the disclosed embodiments are made for purposes of illustration and example only and not limitation. The scope of the present invention should be interpreted by terms of the appended claims.

INDUSTRIAL APPLICABILITY

The optical fingerprint authentication device according to the present invention has a thin structure, includes a various shapes of light source for illumination according to purposes, and can be preferably used for personal authentication using fingerprint patterns in ATM in a bank, a cellular phone, a personal data assistant, a personal computer, and the like.

DESCRIPTION OF REFERENCE NUMERALS 1 transparent base material
2, 9 gas barrier layer
3 anode
3RM raw material for forming anode
4 carrier transporting functional layer group 1
5 light emitting layer
6 carrier transporting functional layer group 2
7 cathode
8 sealing adhesive layer
10 sealing substrate 11 glass substrate
12 light-transmitting region, non-light emitting portion
13 ultraviolet-ray irradiating apparatus
100 fingerprint information reader
F finger
L1 light, irradiation light
L2 reflection light, light signal
M mask
OLED organic EL element
P organic EL panel
S image sensor
U organic functional layer unit
U2 non-light emitting portion (organic functional layer unit)
UV ultraviolet rays

The invention claimed is:

1. An optical fingerprint authentication device which comprises at least a light source and an image sensor and detects diffused light,
wherein the light source is an organic electroluminescence panel,
wherein the organic electroluminescence panel comprises a light emitting portion region and a light-transmitting non-light emitting portion, the light emitting portion region being shaped by an organic electroluminescence element,
wherein the light emitting portion and the light-transmitting non-light emitting portion are disposed in a lateral direction relative to each other, the lateral direction being lateral with respect to the organic electroluminescence panel, and
wherein a fingerprint information reader having the image sensor arranged at a position adjacent to the non-light emitting portion is provided, the fingerprint information reader having the image sensor is disposed directly onto a surface of the light-transmitting non-light emitting portion that is an opposite side from a finger surface side of the organic electroluminescence panel.

2. The optical fingerprint authentication device according to claim 1, wherein the organic electroluminescence element comprises an organic functional layer unit between a pair of electrodes facing each other, one of the electrodes being a light-transmitting electrode, and another of the electrodes being a non-light-transmitting electrode.

3. The optical fingerprint authentication device according to claim 1, wherein the organic electroluminescence element comprises an organic functional layer unit between a pair of electrodes facing each other, each of the electrodes being a light-transmitting electrode.

4. The optical fingerprint authentication device according to claim 2, wherein the light-transmitting electrode comprises an oxide semiconductor or a thin film of a metal or an alloy.

5. The optical fingerprint authentication device according to claim 2, wherein the light-transmitting non-light emitting portion comprises a light-transmitting electrode.

6. The optical fingerprint authentication device according to claim 2, wherein the light-transmitting non-light emitting portion comprises the light-transmitting electrode and the organic functional layer unit.

7. The optical fingerprint authentication device according to claim 1, wherein the organic electroluminescence panel comprises:
an organic electroluminescence element having a continuous structure arranged at a peripheral portion; and
the light-transmitting non-light emitting portion at a center portion.

8. The optical fingerprint authentication device according to claim 1,
wherein the organic electroluminescence panel comprises a plurality of organic electroluminescent elements which are arranged in parallel in a stripe shape, and
wherein the light-transmitting non-light emitting portion is formed between the organic electroluminescent elements which are in a stripe shape.

9. The optical fingerprint authentication device according to claim 1, wherein the organic electroluminescence panel comprises:
a plurality of independent organic electroluminescent elements arranged separately at a peripheral portion, and
the light-transmitting non-light emitting portion at a center portion.

10. The optical fingerprint authentication device according to claim 1, wherein the organic electroluminescence panel emits light which has a wavelength in a visible light region.

11. The optical fingerprint authentication device according to claim 1, wherein the organic electroluminescence panel emits light which has a wavelength in an infrared region.

12. The optical fingerprint authentication device according to claim 1, wherein at least one of an organic functional layer unit, a cathode, and an anode of the light emitting portion region is not present in the light-transmitting non-light emitting portion or the organic functional layer unit in the light-transmitting non-light emitting portion is deactivated.

13. The optical fingerprint authentication device according to claim 1, wherein the organic electroluminescence element includes an anode, a cathode, and an organic functional layer unit.

14. The optical fingerprint authentication device according to claim 13, wherein the anode, the cathode, and the organic functional layer unit are not present in the light-transmitting non-light emitting portion, and
the light-transmitting non-light emitting portion includes a sealing adhesion layer in a space laterally adjacent to the anode, the cathode, and the organic functional layer unit.

15. The optical fingerprint authentication device according to claim 13, wherein at least one of the anode, the cathode, and the organic functional layer unit extends across the light-transmitting non-light emitting portion.

16. The optical fingerprint authentication device according to claim 13, wherein the organic functional layer unit extends across the light-transmitting non-light emitting portion and the organic functional layer unit is deactivated in the light-transmitting non-light emitting portion.

17. The optical fingerprint authentication device according to claim 1, wherein a sealing substrate encompasses both the light emitting portion and the light-transmitting non-light emitting portion.

* * * * *